(12) United States Patent
Cairns

(10) Patent No.: US 8,944,082 B2
(45) Date of Patent: Feb. 3, 2015

(54) DUAL RESERVOIR COUPLER

(75) Inventor: James Cairns, Ormond Beach, FL (US)

(73) Assignee: Teledyne Instruments, Inc., Thousand Oaks, CA (US)

( * ) Notice: Subject to any disclaimer, the term of this patent is extended or adjusted under 35 U.S.C. 154(b) by 594 days.

(21) Appl. No.: 13/296,406

(22) Filed: Nov. 15, 2011

(65) Prior Publication Data
US 2012/0125460 A1 May 24, 2012

Related U.S. Application Data

(60) Provisional application No. 61/415,972, filed on Nov. 22, 2010.

(51) Int. Cl.
*F16L 37/00* (2006.01)
*F16L 29/00* (2006.01)
*A61M 39/18* (2006.01)

(52) U.S. Cl.
CPC .............. *F16L 29/005* (2013.01); *A61M 39/18* (2013.01); *F16L 2201/44* (2013.01)
USPC ..................... 137/1; 137/614.02; 137/614.05; 251/149.1

(58) Field of Classification Search
USPC ................. 137/614.02–614.05, 1; 251/149.1, 251/149.6
See application file for complete search history.

(56) References Cited

U.S. PATENT DOCUMENTS

| | | | |
|---|---|---|---|
| 3,279,497 A | 10/1966 | Norton et al. | |
| 3,839,608 A | 10/1974 | De Vries | |
| 4,142,770 A | 3/1979 | Butler, Jr. et al. | |
| 4,249,572 A * | 2/1981 | Shindelar et al. | 137/614.04 |
| 4,335,747 A | 6/1982 | Mitsumoto et al. | |
| 4,496,959 A | 1/1985 | Frerichs | |
| 4,682,848 A | 7/1987 | Cairns et al. | |
| 4,696,540 A | 9/1987 | Adams et al. | |
| 4,889,527 A | 12/1989 | Herrli | |
| 5,293,902 A | 3/1994 | Lapierie | |
| 5,334,032 A | 8/1994 | Myers et al. | |
| 5,496,300 A | 3/1996 | Hirsch et al. | |
| 5,536,262 A | 7/1996 | Velasquez | |

(Continued)

FOREIGN PATENT DOCUMENTS

EP 0538089 11/1997

OTHER PUBLICATIONS

Search Report and Written Opinion for corresponding International Application No. PCT/US2011/60700 dated Mar. 9, 2012.

*Primary Examiner* — Kevin Lee
(74) *Attorney, Agent, or Firm* — Procopio Cory Hargreaves & Savitch LLP

(57) ABSTRACT

A coupler mechanism comprising plug and receptacle units sealably mates and de-mates first and second reservoirs. In the mating sequence, the plug and receptacle units are brought together so that their end-seals are pressed tightly against each other axially, thus forming a sealed barrier between the units and the outside environment. Once the face-to-face seal between the units has been established, further engagement displaces slidable seal elements laterally, thereby creating an opening between the reservoirs, the opening remaining sealed from the outside environment before, during and after mating. The sequence for demating the units is just the reverse of the mating sequence. One embodiment of the invention applies the aforementioned construction to harsh-environment electrical, fiber-optical, and hybrid electro-optical connectors.

73 Claims, 21 Drawing Sheets

(56) References Cited

U.S. PATENT DOCUMENTS

| | | |
|---|---|---|
| 5,645,438 A | 7/1997 | Cairns |
| 5,645,442 A | 7/1997 | Cairns |
| 5,685,727 A | 11/1997 | Cairns |
| 5,738,535 A | 4/1998 | Cairns |
| 5,746,248 A | 5/1998 | Tobiasz |
| 5,838,857 A | 11/1998 | Niekrasz |
| 6,017,227 A | 1/2000 | Cairns |
| 6,095,838 A | 8/2000 | Brickett |
| 6,196,854 B1 | 3/2001 | Hand |
| 6,322,787 B1 | 11/2001 | Mocikat et al. |
| 6,332,787 B1 | 12/2001 | Barlow et al. |
| 6,354,564 B1 | 3/2002 | Van Scyoc et al. |
| 6,439,778 B1 | 8/2002 | Cairns |
| 6,443,764 B2 | 9/2002 | Makita |
| 6,464,405 B2 | 10/2002 | Cairns et al. |
| 6,561,268 B2 | 5/2003 | Jones |
| 6,736,545 B2 | 5/2004 | Cairns et al. |
| 7,004,638 B2 | 2/2006 | Nicholson |
| 7,097,515 B2 | 8/2006 | Siddiqi et al. |
| 7,112,080 B2 | 9/2006 | Nicholson |
| 7,244,132 B1 | 7/2007 | Cairns et al. |
| 7,364,448 B2 | 4/2008 | Cairns et al. |
| 7,442,081 B2 | 10/2008 | Burke et al. |
| 7,481,584 B2 | 1/2009 | Cairns |
| 7,618,198 B2 | 11/2009 | Baxter et al. |
| 7,648,285 B2 | 1/2010 | Maletzky et al. |
| 7,695,301 B2 | 4/2010 | Mudge, III et al. |
| 7,959,454 B2 | 6/2011 | Ramasubramanian et al. |
| 7,988,368 B2 | 8/2011 | Sakurai et al. |
| 7,988,476 B2 | 8/2011 | Billman et al. |
| 8,123,549 B2 | 2/2012 | Jazowski et al. |
| 2005/0022883 A1 | 2/2005 | Adams et al. |
| 2009/0080836 A1 | 3/2009 | Cairns et al. |
| 2011/0000677 A1 | 1/2011 | Overfield |
| 2011/0304135 A1 | 12/2011 | Chaize |

\* cited by examiner

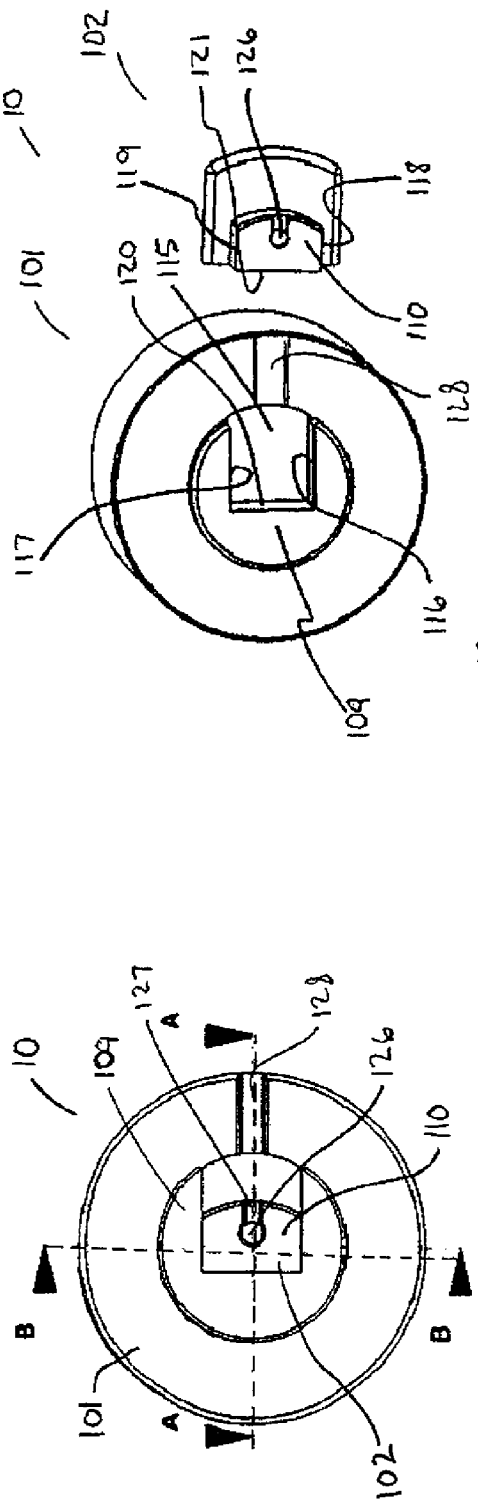
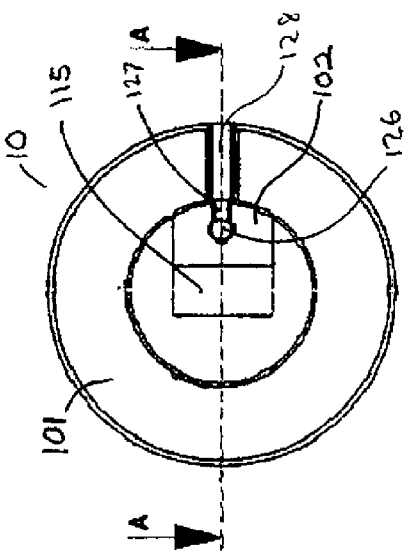
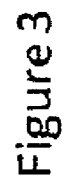
Figure 1
Figure 2
Figure 3

Section B-B of Figure 1

Section A-A of Figure 1

Section A-A of Figure 3

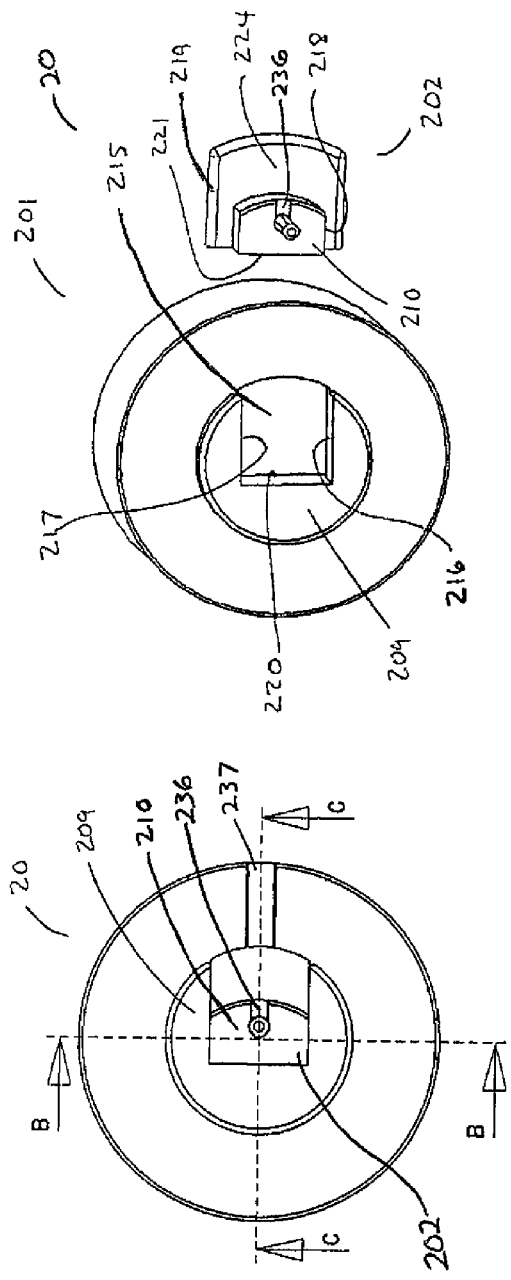
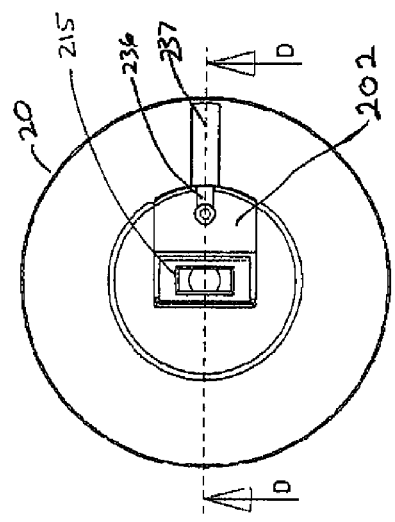
Figure 9
Figure 10
Figure 8

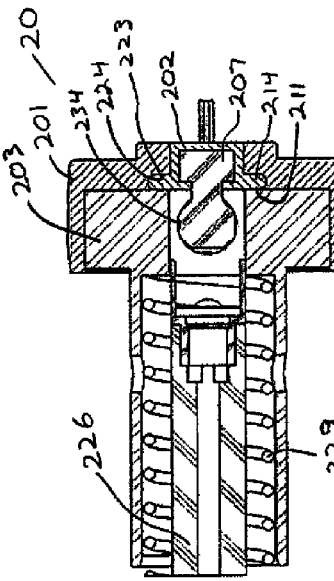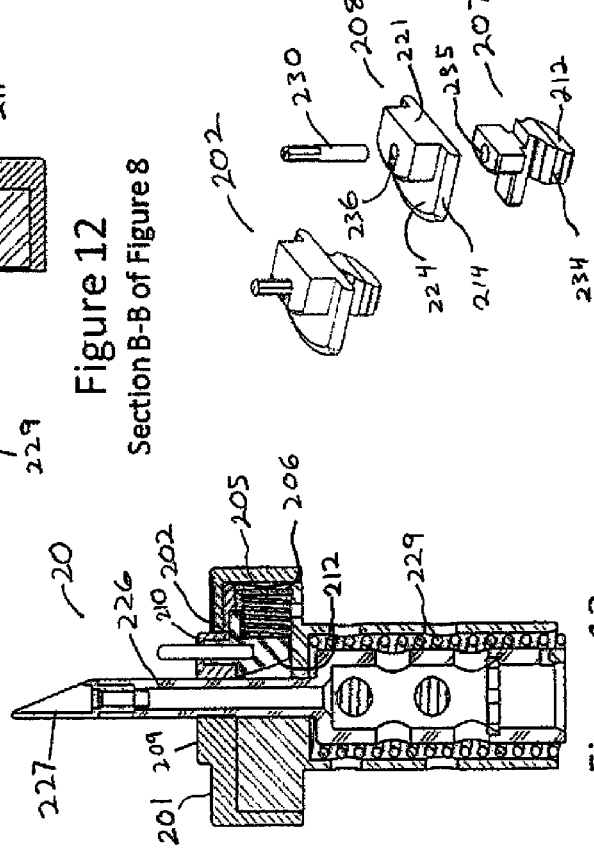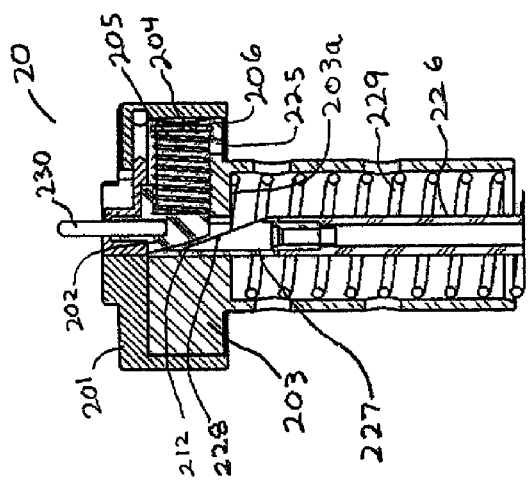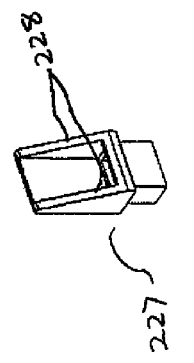

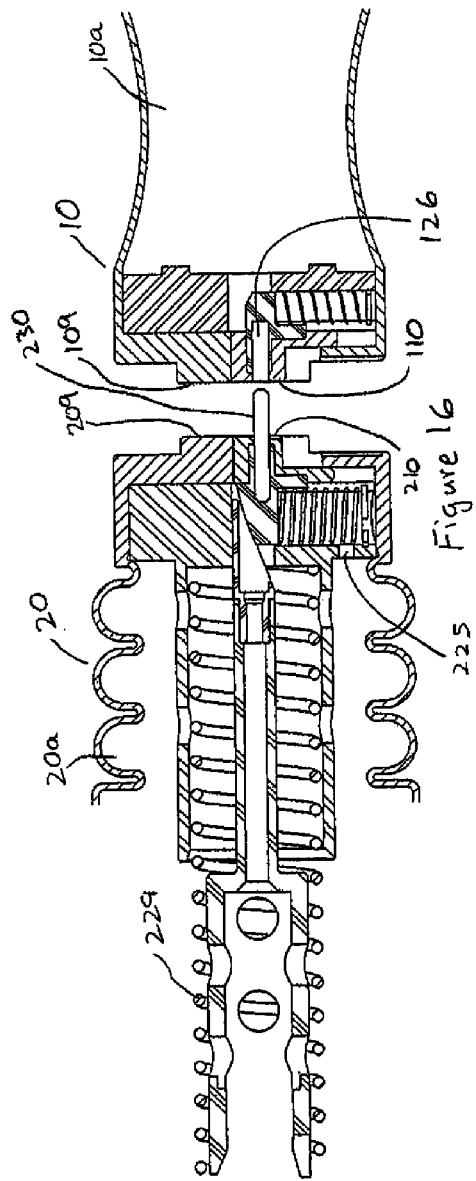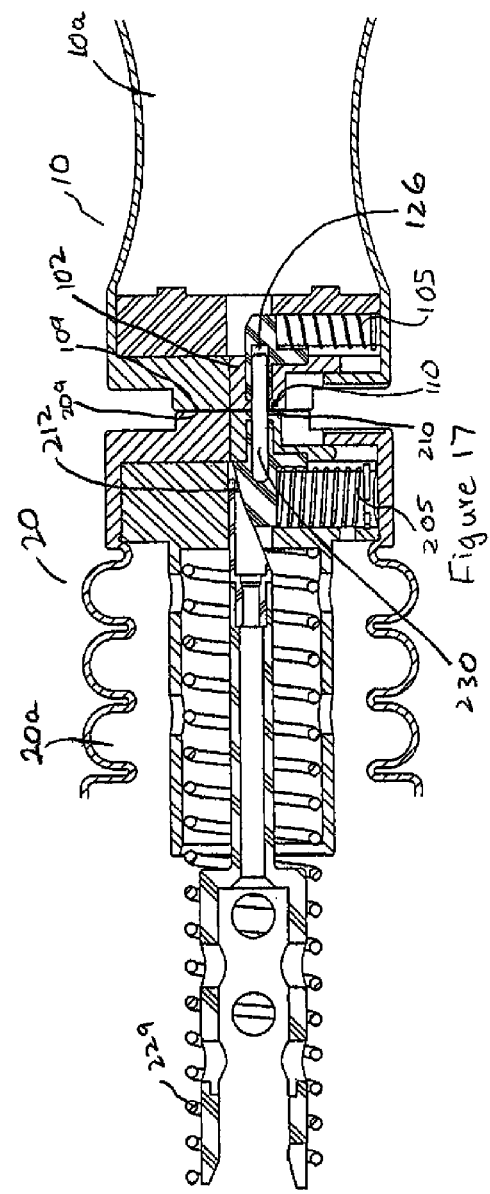

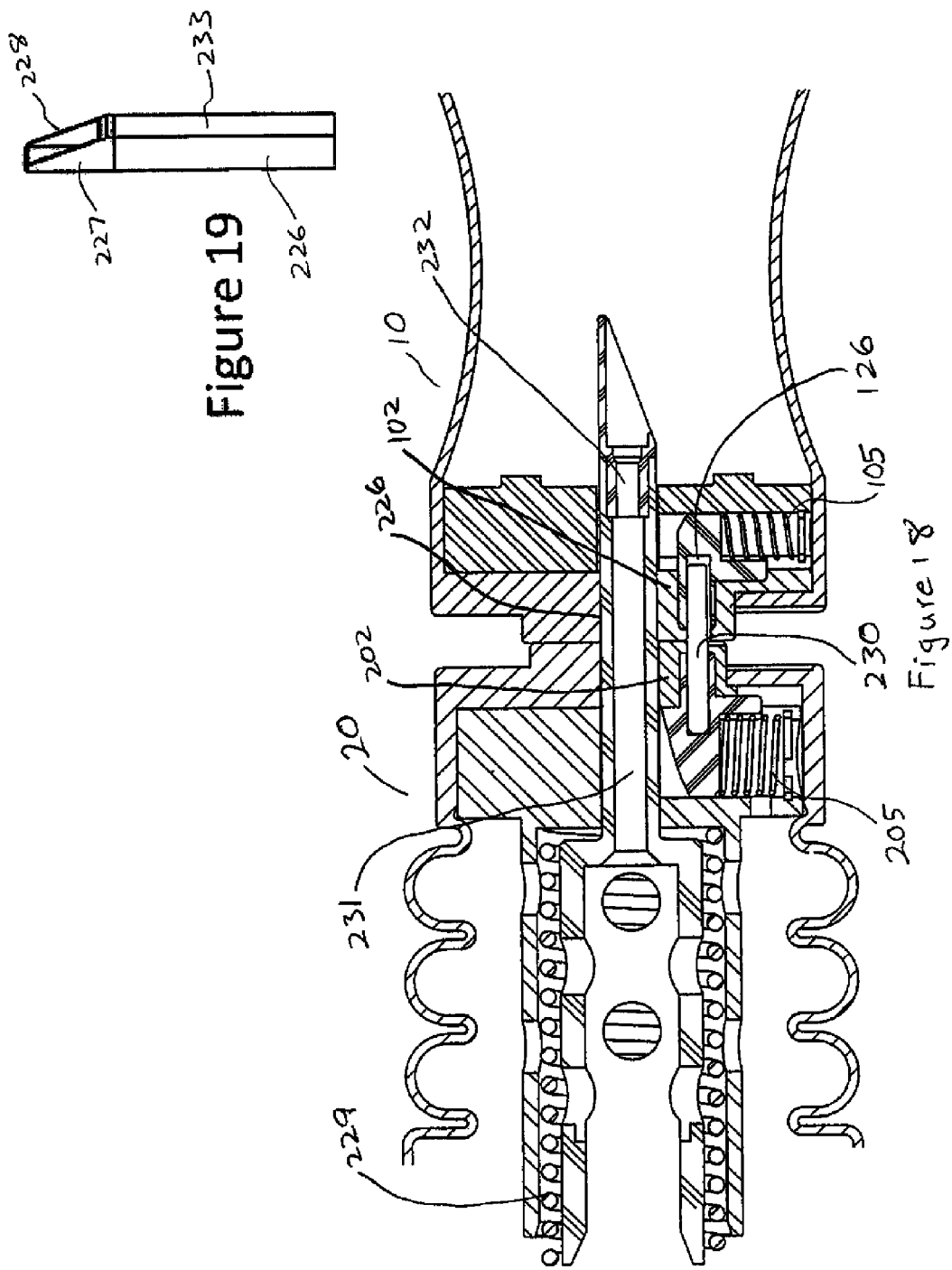

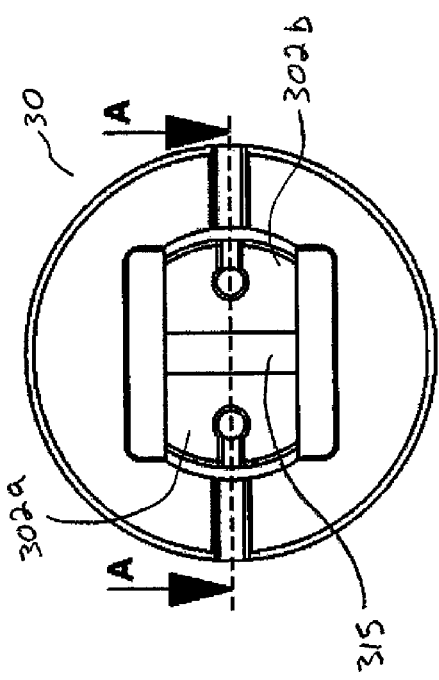
Figure 22
Section A – A of Figure 21
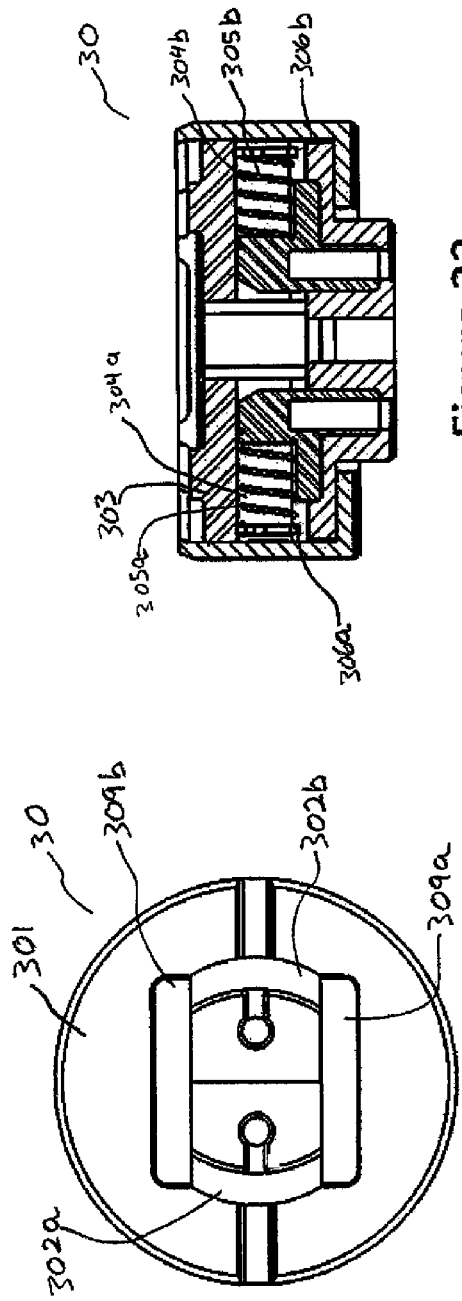
Figure 20
Figure 21

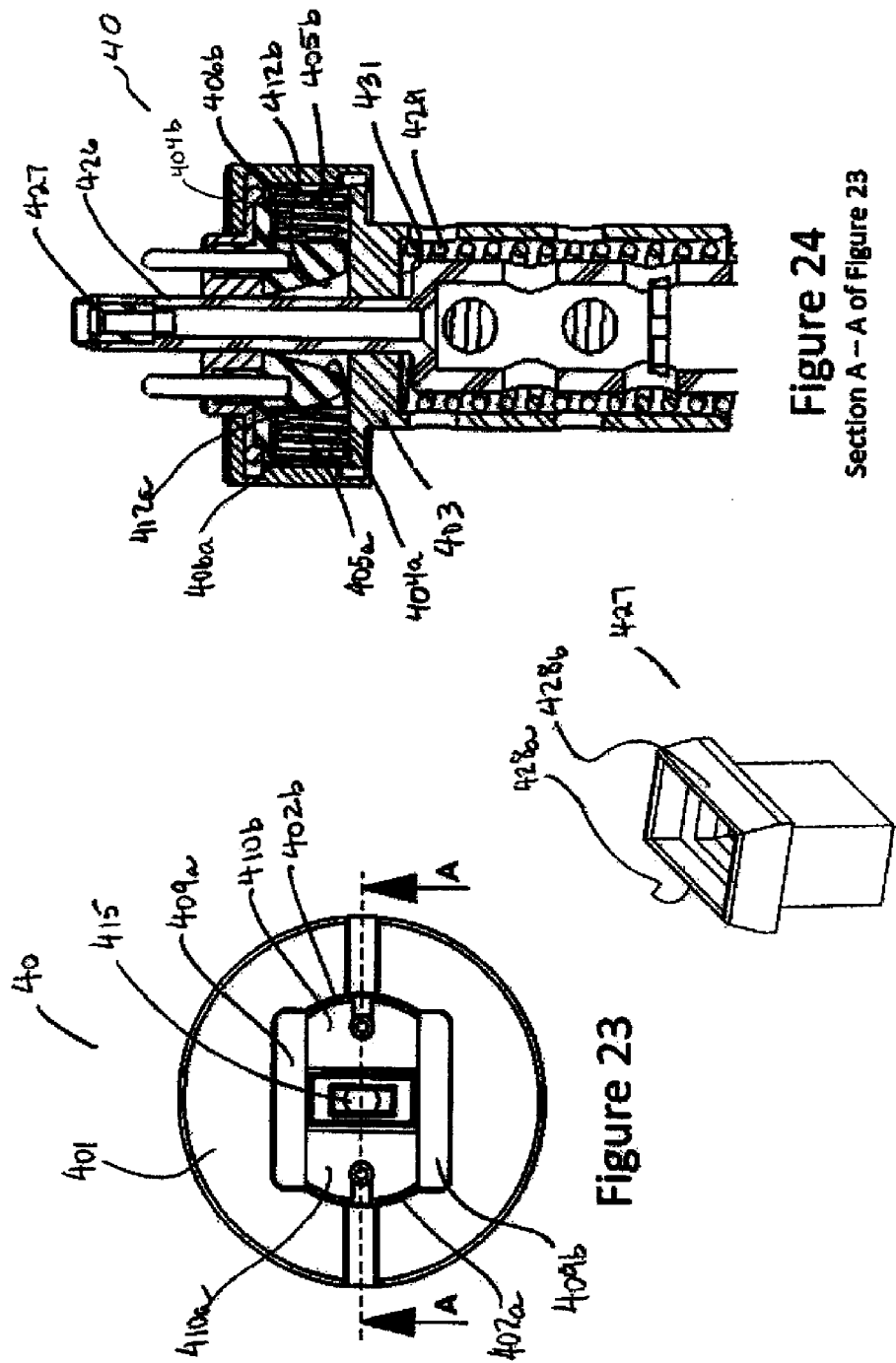

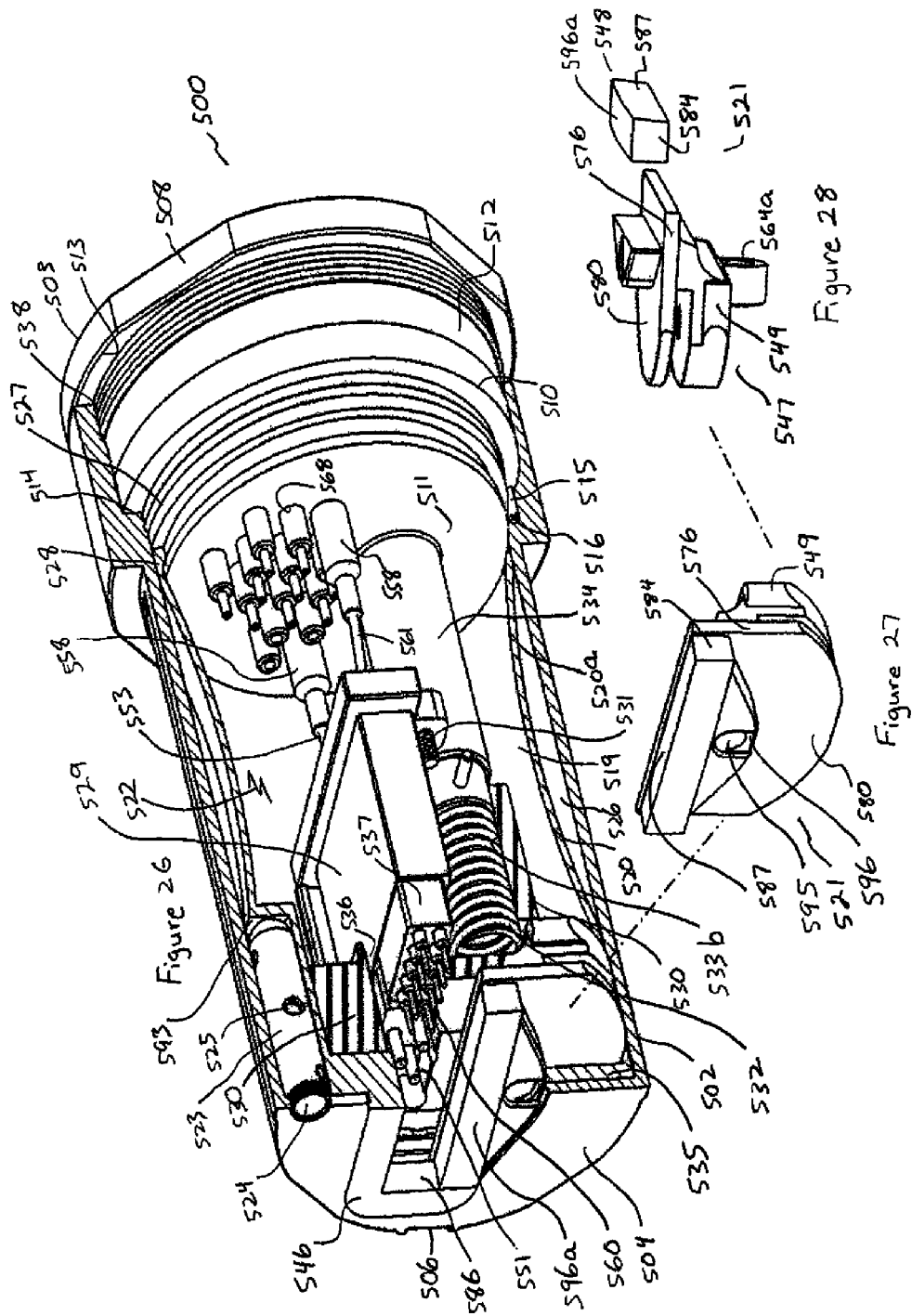

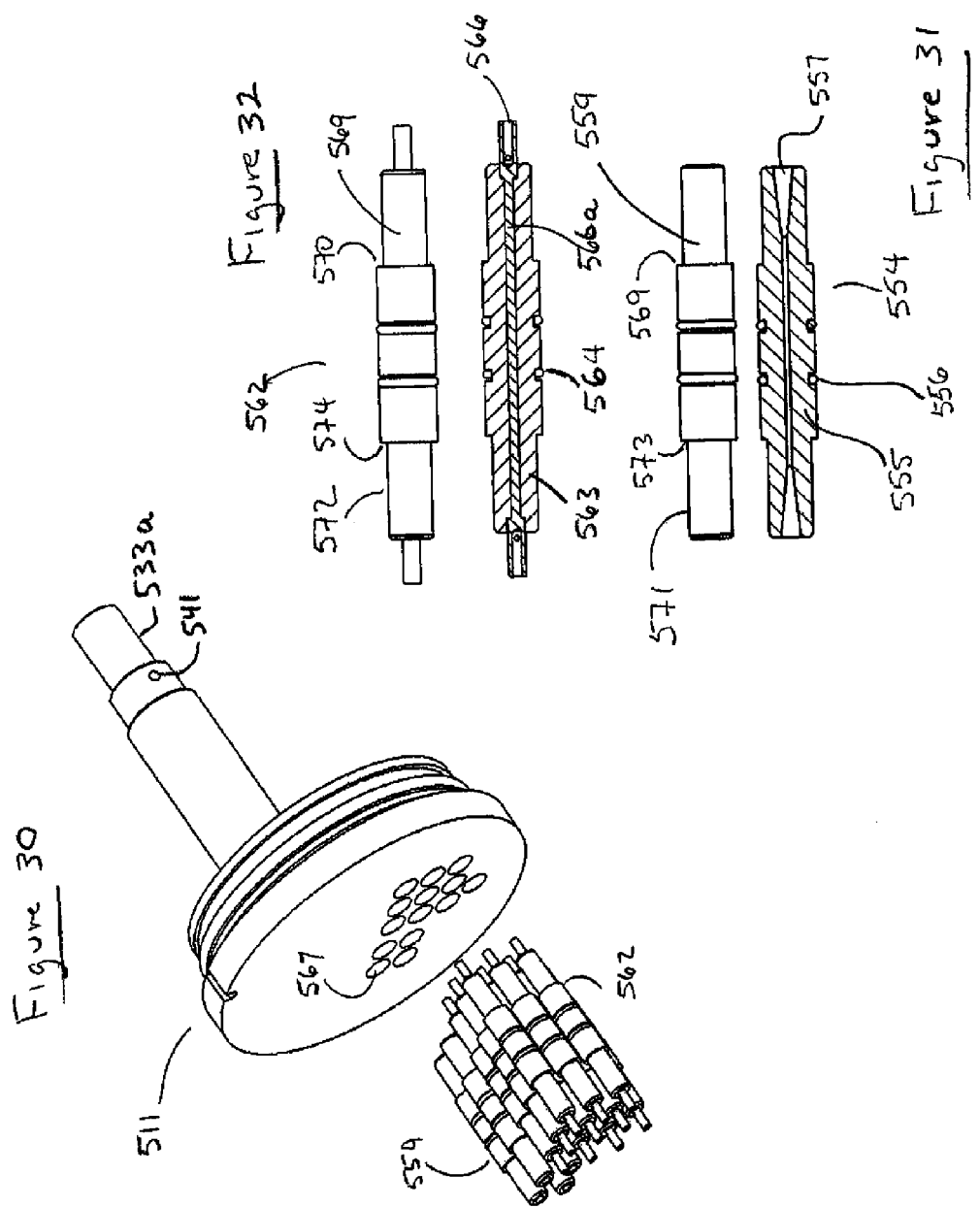

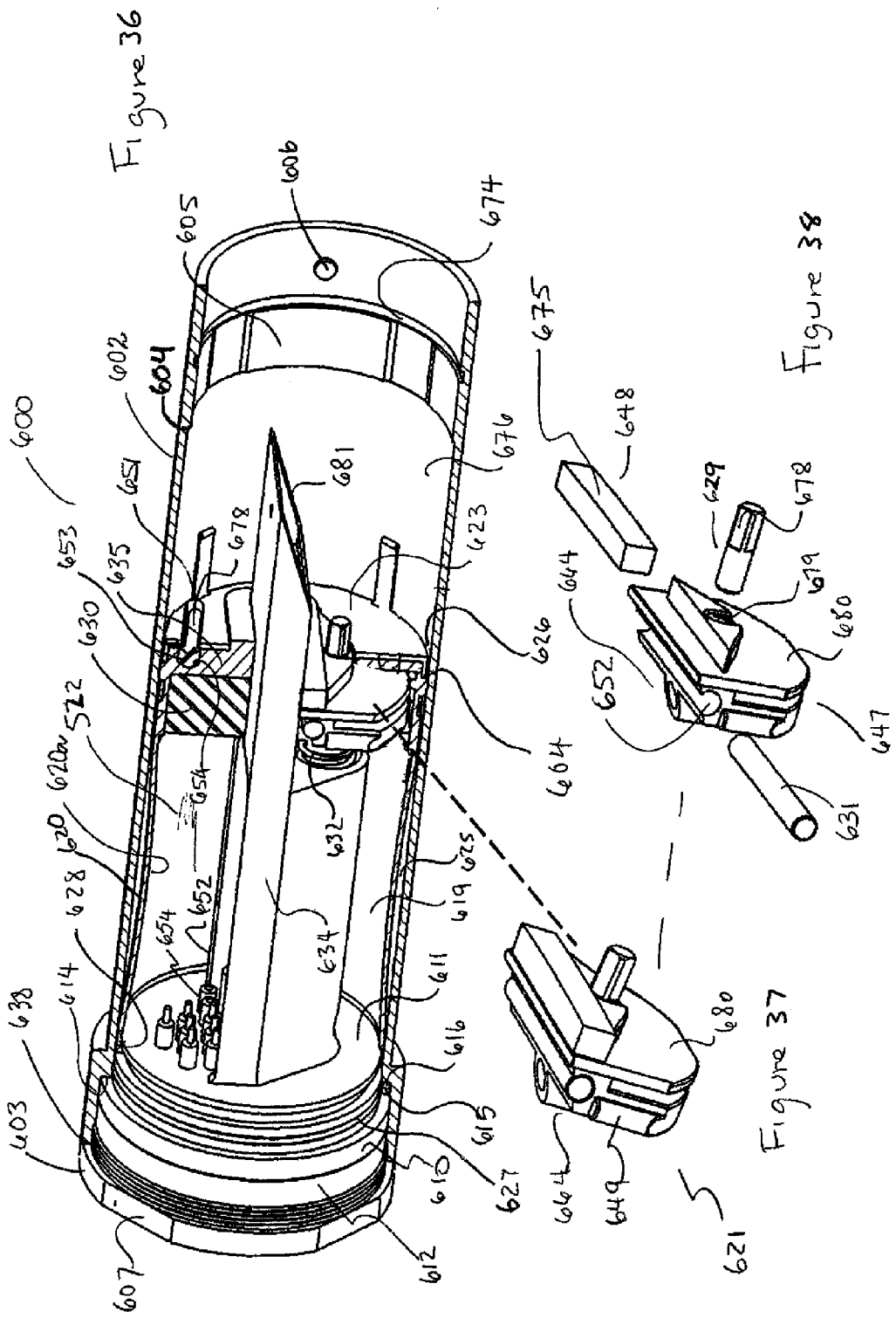

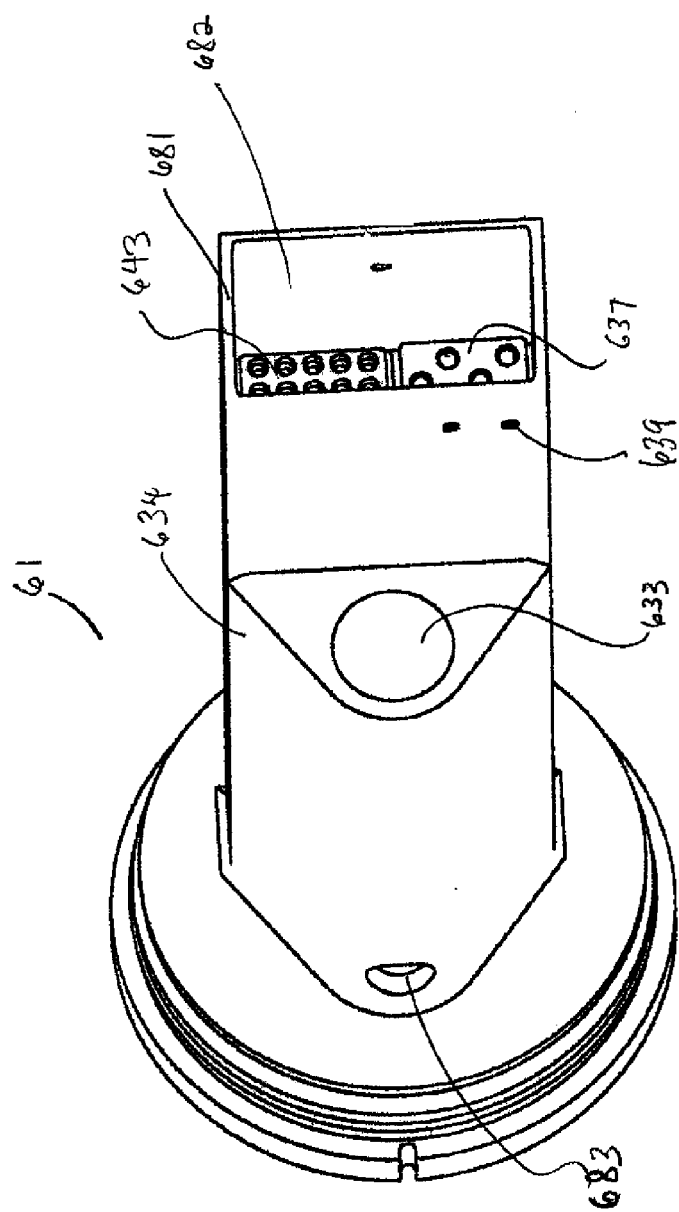

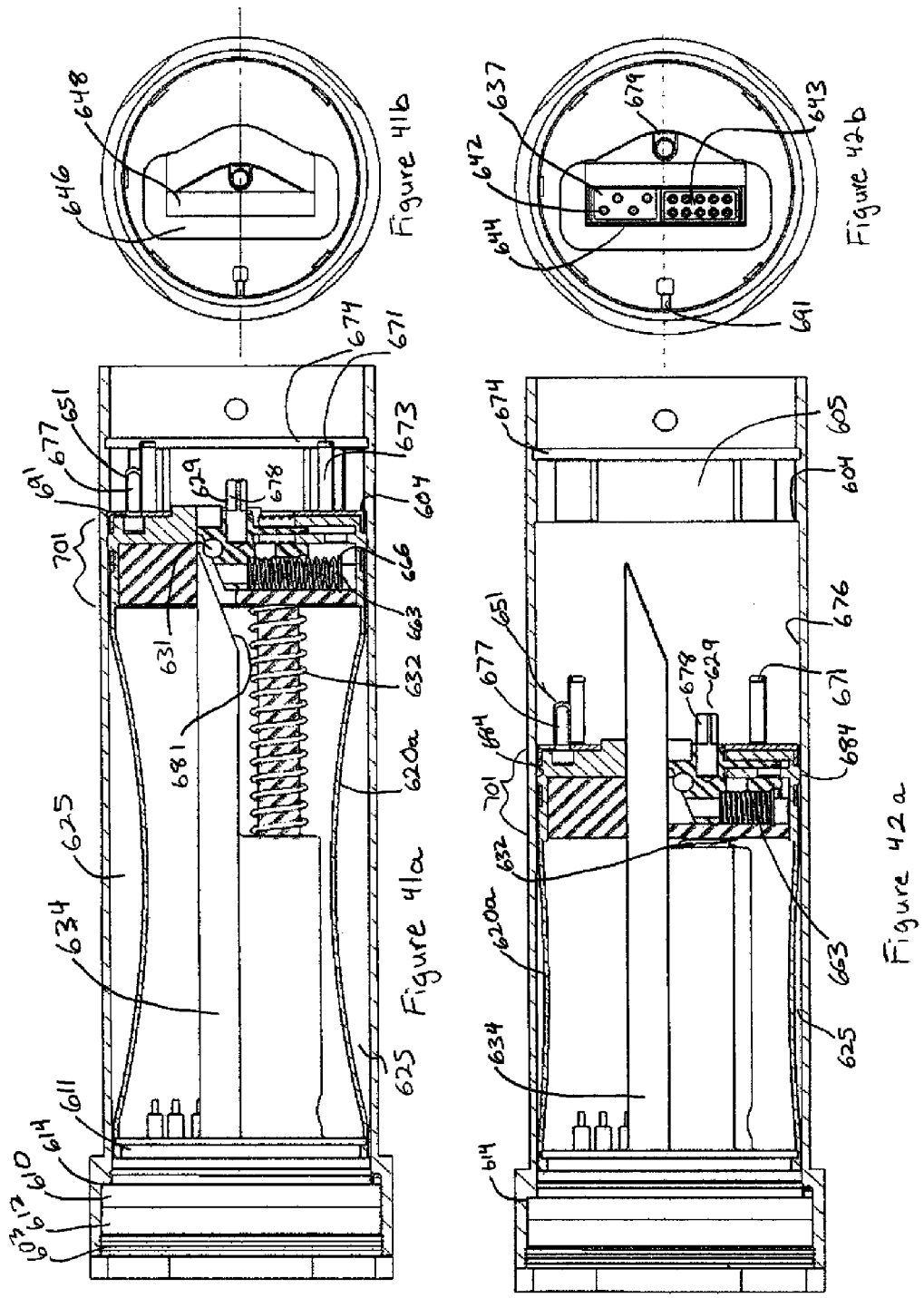

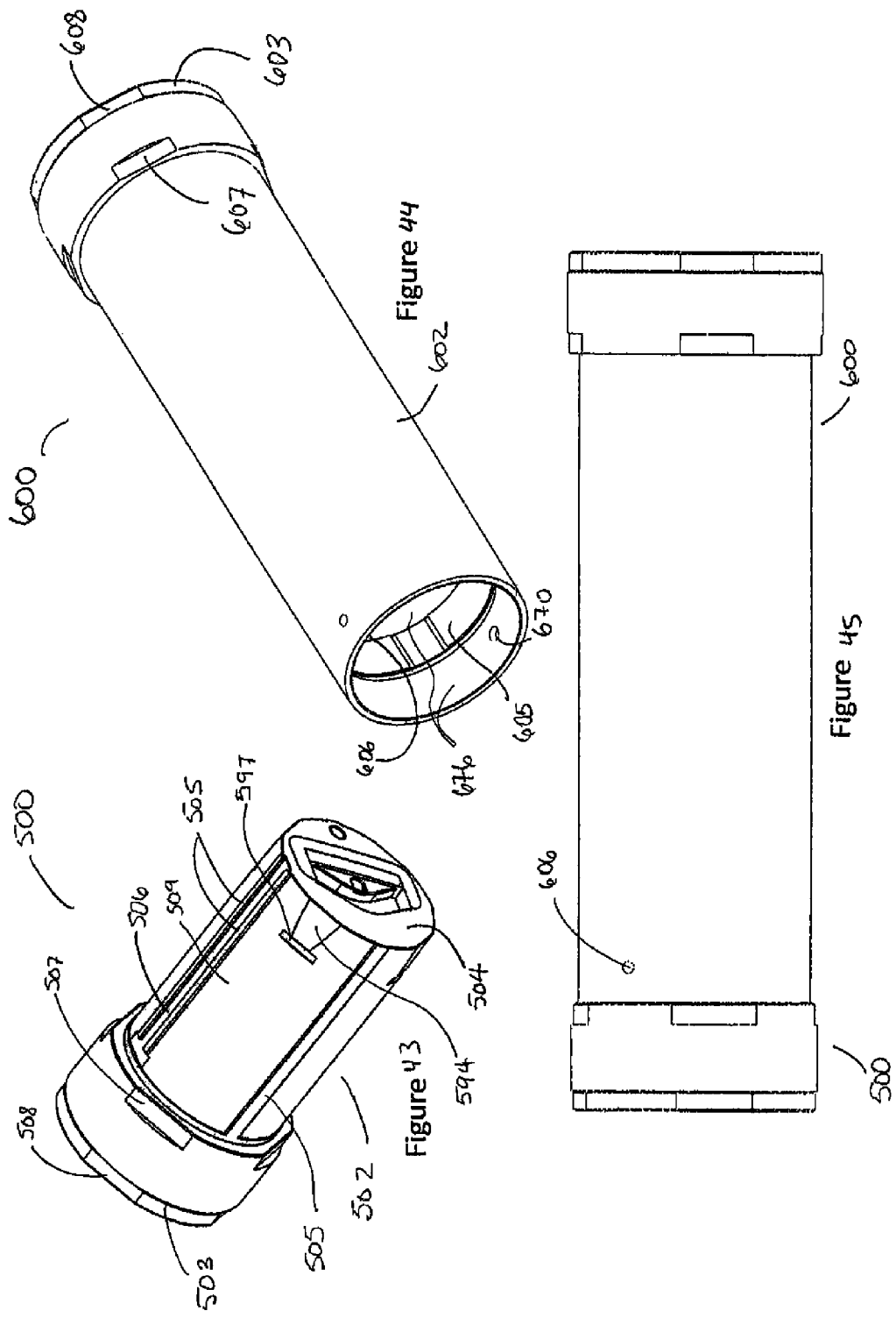

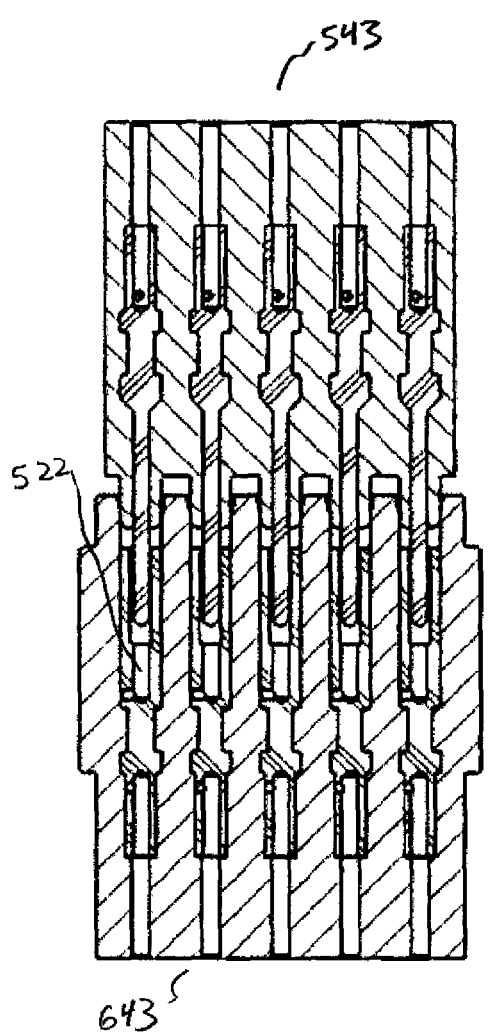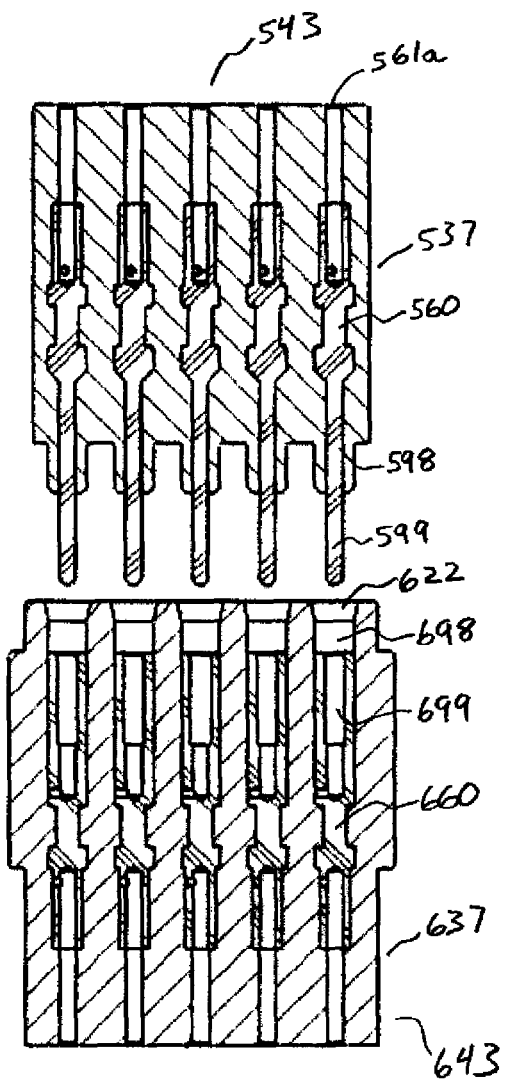
Figure 48
Figure 47

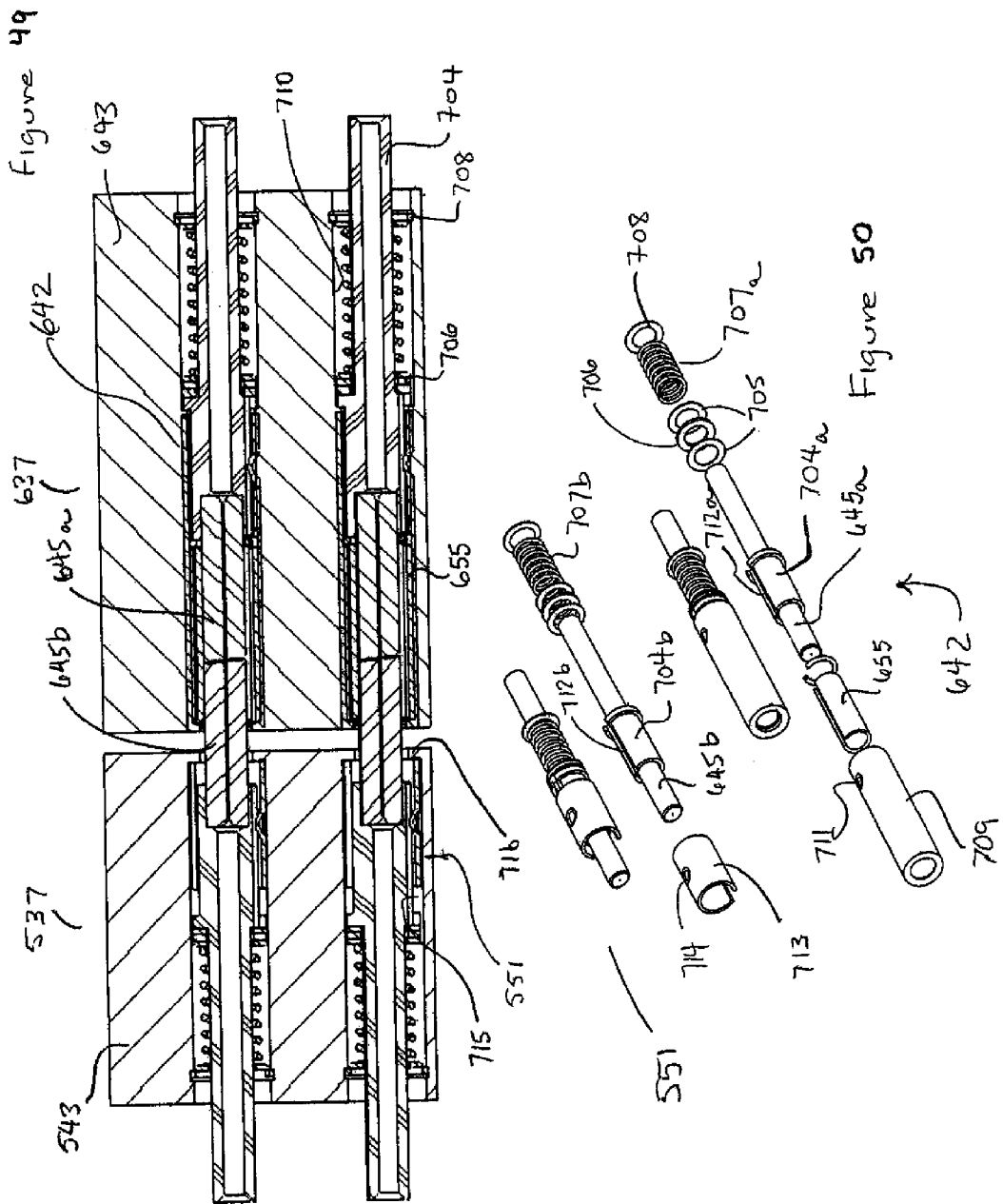

DUAL RESERVOIR COUPLER

CROSS-REFERENCE TO RELATED APPLICATIONS

This application claims the benefit under 35 U.S.C. §119 (e) of the earlier filing date of U.S. Provisional Application Ser. No. 61/415,972 filed on Nov. 22, 2010 the contents of which are hereby incorporated by reference.

FIELD OF THE INVENTION

Embodiments of the invention include an apparatus and method for joining two fluid reservoirs in such a manner that the contents of the reservoirs remain sealed from the outside environment before, during, and after coupling and subsequent decoupling.

BACKGROUND OF THE INVENTION

There are applications with requirements to sealably join two reservoirs while simultaneously opening a communication path between the reservoirs such as might be required to add a reagent to a chemical mixture, or for connecting reservoirs of toxic fluids or gasses which cannot interact with the surrounding environment. Some industrial examples are given in U.S. Pat. Nos. 3,279,497; 4,496,959; 5,293,902; and 6,354,564, the disclosures of which are incorporated by reference herein.

In the medical field, there are requirements to sealably connect and disconnect fluid reservoirs without contamination of the outside environment by the contents of the reservoirs, or vice-versa. Such reservoirs may consist of tubes, sacs, vials, bottles, etc. Some examples are given in U.S. Pat. Nos. 3,279,497; 4,496,959; 5,293,902; and 6,354,564, the disclosures of which are incorporated by reference herein. Some medical-use examples are given in U.S. Pat. Nos. 4,889,527; 5,496,300; and 5,536,262, the disclosures of which are incorporated by reference herein.

Many applications in the offshore industries require connectors that can be repeatedly mated and de-mated in hostile environments, such as seawater. These wet-mateable connectors include electrical connectors, fiber-optical connectors and hybrid electro-optical connectors. Some examples of wet-mateable connectors are described in U.S. Pat. Nos. 4,682,848; 5,685,727; 5,738,535; 5,838,857; 6,017,227; 6,095,838; 6,322,787; 6,736,545; 7,004,638; 7,244,132; 7,648,285; US Patent Application 20090080836, and EPO Patent 0538089A1, the disclosures of which are incorporated by reference herein.

SUMMARY OF THE INVENTION

According to embodiments of the invention, an apparatus is provided which includes a first unit (called for convenience the "plug") in communication with a first reservoir and a second unit (called for convenience a "receptacle") in communication with a second reservoir which are repeatedly mateable together and subsequently de-mateable while their respective reservoirs remain sealed from the environment in which they are operated. A connector embodiment herein described is intended for underwater use, although similar embodiments of the coupler described herein could be used for many diverse environments such as medical and other environments.

Three embodiments of the invention are described herein. The first two described embodiments illustrate a coupler apparatus for sealably coupling two simple reservoirs. The third-described embodiment of the invention illustrates the coupler apparatus configured to connect electrical and or fiber optical junctions in a harsh environment such as seawater. In this third embodiment of the invention, a plug unit houses a first one or a plurality of contact junctions within a first reservoir sealed from the external environment. The receptacle unit houses a respective second one or a plurality of contact junctions within a second reservoir sealed from the external environment. When the plug and receptacle units are mated, the first and second reservoirs are sealably joined together, thereby joining the respective first one or a plurality of contact junctions and respective second one or a plurality of contact junctions. When the units are subsequently demated the first and second chambers are once again separately sealed from the operating environment. Although the third coupler embodiment is described herein in the context of a connector for underwater use, similar embodiments of the coupler apparatus could be used for many diverse applications such as are encountered in medical and industrial fields.

BRIEF DESCRIPTION OF THE DRAWINGS

The invented coupling mechanism is first described herein in general terms without regard to specific applications. It will be easily understood that the coupler can be readily adapted to a wide variety of housings and reservoir types. It will also be understood that multiple couplers can be ganged so as to simultaneously couple multiple reservoirs, as is often done in automatic dispensing equipment, for instance. FIGS. 1 through 19 describe a first embodiment of a coupling mechanism that permits two closed, independent reservoirs to be joined and subsequently separated while remaining at all times sealed from the in-situ environment. FIGS. 20 through 25 describe a second embodiment of the invented coupling mechanism. FIGS. 26 through 50 demonstrate the third coupling mechanism embodiment configured for use as a hybrid electro-optical connector. The details of the present invention, both as to its structure and operation, may be gleaned in part by study of the accompanying drawings, in which like reference numerals refer to like parts, and in which:

FIG. 1 is mating-face view of the receptacle end-seal in the unmated (closed) condition;

FIG. 2 shows the sliding element of the receptacle end-seal juxtaposed with the fixed element;

FIG. 3 is mating-face view of the receptacle end-seal in the mated (open) condition;

FIG. 4 is an axial cross-sectional view of the FIG. 1 receptacle end-seal in the unmated (closed) condition;

FIG. 5 is an axial cross-sectional view of the FIG. 1 receptacle end-seal in the unmated (closed) condition. The view is orthogonal to the FIG. 4 view;

FIG. 6 is an axial cross-sectional view of the FIG. 3 receptacle end-seal in the mated (open) condition;

FIG. 7 shows the sliding element of the receptacle end-seal juxtaposed with the integral spine that supports it;

FIG. 8 is a mating-face view of the plug end-seal in the unmated (closed) condition;

FIG. 9 shows the fixed and sliding elements of the plug end-seal juxtaposed;

FIG. 10 is a mating-face view of the plug end-seal in the mated (open) condition;

FIG. 11 is an axial cross-sectional view of the FIG. 8 plug end-seal in the unmated (closed) condition;

FIG. 12 is an axial cross-sectional view the FIG. 8 plug end-seal in the unmated (closed) condition. The view is orthogonal to the FIG. 11 view;

FIG. 13 is an axial cross-sectional view of the FIG. 10 plug end-seal in the mated (open) condition;

FIG. 14 is an enlarged view of the plug stem actuator tip;

FIG. 15 shows the sliding sub-assembly element of the plug end-seal juxtaposed with the integral spine that supports it, and with the actuator pin;

FIG. 16 is an axial cross-sectional view of the plug and receptacle end-seals juxtaposed in position just prior to mating;

FIG. 17 is an axial cross-sectional view of the plug and receptacle end-seals in position just as mating begins;

FIG. 18 is an axial cross-sectional view of the plug and receptacle end-seals in position when fully mated;

FIG. 19 depicts the anterior portion of the plug stem with the actuator tip mounted in position;

FIG. 20 is mating-face view of the second-embodiment receptacle end-seal in the unmated (closed) condition;

FIG. 21 is mating-face view of the second-embodiment receptacle end-seal in the mated (open) condition;

FIG. 22 is an axial cross-sectional view of the FIG. 21 receptacle end-seal in the mated (open) condition;

FIG. 23 is mating-face view of the second-embodiment plug end-seal in the mated (open) condition;

FIG. 24 is an axial cross-sectional view of the FIG. 23 plug end-seal in the mated (open) condition;

FIG. 25 is an enlarged view of the second-embodiment plug stem actuator tip;

FIG. 26 is a partial axial cross-sectional view of the connector receptacle unit of a hybrid electro-optical connector;

FIG. 27 shows the receptacle sliding end-seal assembly of the hybrid electro-optical connector;

FIG. 28 is an exploded view of the receptacle end-seal assembly of the hybrid electro-optical connector;

FIG. 29 in an exploded view of the connector receptacle unit of the hybrid electro-optical connector;

FIG. 30 is an exploded view of the receptacle base assembly consisting of the receptacle base and optical and electrical penetrators of the hybrid electro-optical connector;

FIG. 31 illustrates a typical optical penetrator;

FIG. 32 shows a typical electrical penetrator;

FIG. 33 is a partial axial cross-section of the anterior portion of the receptacle bladder of the hybrid electro-optical connector;

FIG. 34 is a partial cross-section of the receptacle end-seal in the open position of the hybrid electro-optical connector;

FIG. 35 is a partial cross-section of the receptacle end-seal in the closed position of the hybrid electro-optical connector;

FIG. 36 is a partial axial cross-sectional view of the connector plug unit of the hybrid electro-optical connector;

FIG. 37 shows the plug sliding end-seal assembly of the hybrid electro-optical connector;

FIG. 38 is an exploded view of the plug end-seal assembly of the hybrid electro-optical connector;

FIG. 39 in an exploded view of the connector plug unit of the hybrid electro-optical connector;

FIG. 40 shows the plug base assembly of the hybrid electro-optical connector;

FIG. 41a is a partial axial half-section of the plug connector unit in the un-mated condition;

FIG. 41b is a front-end view of the plug connector unit in the un-mated condition;

FIG. 42a is a partial axial half-section of the plug connector unit in the mated condition;

FIG. 42b is a front-end view of the plug connector unit in the mated condition;

FIG. 43 is a perspective view of the connector receptacle unit;

FIG. 44 is a perspective view of the connector plug unit;

FIG. 45 is a side view of the mated connector plug and receptacle units;

FIG. 46 is a partial axial cross-sectional view of the mated connector plug and receptacle unit end-seals;

FIG. 47 is an axial cross-sectional view taken through a plane of electrical junctions of the plug and receptacle electrical contact blocks in the unmated condition;

FIG. 48 is an axial cross-sectional view taken through a plane of electrical junctions of the plug and receptacle electrical contact blocks in the mated condition;

FIG. 49 is an axial cross-sectional view taken through a plane of optical junctions of the plug and receptacle optical contact blocks in the mated condition; and FIG. 50 shows exploded views of the plug and receptacle optical contact assemblies.

DETAILED DESCRIPTION OF THE INVENTION

Figure 3A:
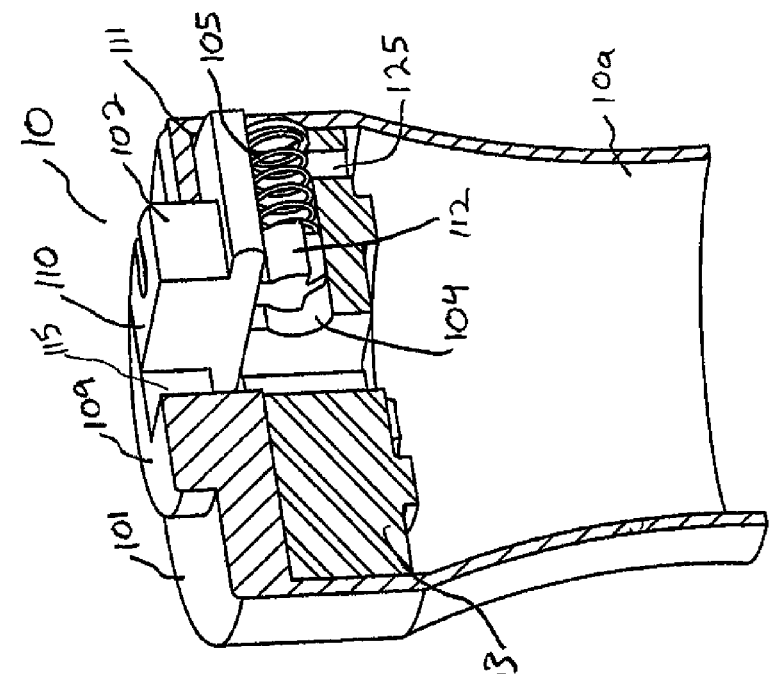
FIG. 3a is a partial cross-sectional perspective view of the receptacle end-seal in the mated (open) condition.

It is to be understood that the figures and descriptions of the present invention have been simplified to illustrate elements that are relevant for a clear understanding of the invention, while eliminating, for purposes of clarity, other elements that may be well known. Those of ordinary skill in the art will recognize that other elements are desirable and/or required in order to implement the invention. However, because such elements are known in the art, and because they do not facilitate a better understanding of the present invention, a discussion of such elements is not provided herein. The detailed description will be provided herein below with reference to the attached drawings.

For purposes of the description hereinafter, the terms "upper", "lower", "vertical", "horizontal", "axial", "top", "bottom", and derivatives thereof shall relate to the invention, as it is oriented in the drawings. However, it is to be understood that the invention may assume various alternative configurations except where expressly specified to the contrary. It is also to be understood that the specific elements illustrated in the drawings and described in the following specification are simply exemplary embodiments of the invention. Therefore, specific dimensions, orientations and other physical characteristics related to the embodiments disclosed herein are not to be considered limiting.

A first embodiment in accordance with the present invention will be described below with reference to the accompanying drawings. FIGS. 1 through 19 describe an embodiment of a coupling mechanism that permits two closed, independent reservoirs to be joined and subsequently separated while remaining at all times sealed from the in-situ environment. The reservoirs may be any receptacle or chamber such as tubes, sacs, vials, bottles, etc. The reservoirs 10a and 20a (FIGS. 16, 17) are coupled together by respective first and second coupler units in the form of a receptacle end-seal assembly 10 and a plug end-seal assembly 20 discussed in more detail below. Alternatively, the coupler units described herein could be used to couple a reservoir to the surrounding environment.

Figure 4:
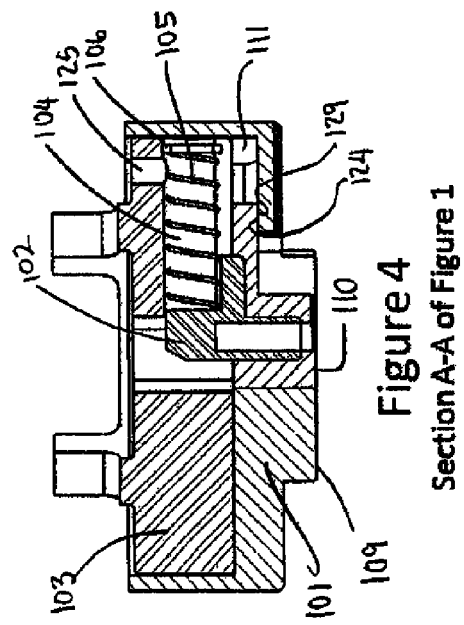
Figure 6:
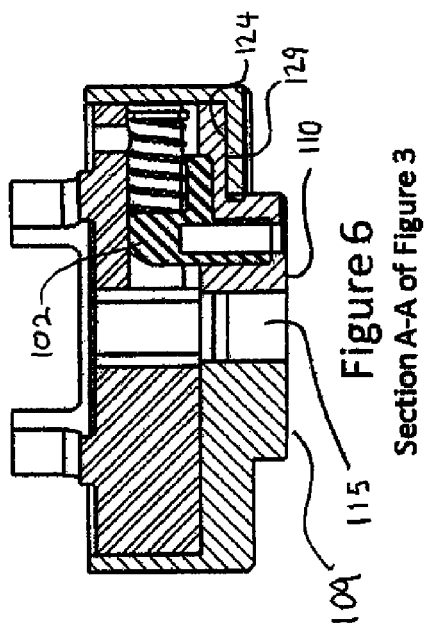

The first embodiment of FIGS. 1-19 includes receptacle end-seal assembly 10, the details of which are shown in FIGS. 1-7, which is mateable with plug end-seal assembly 20, the details of which are shown in FIGS. 8-15. Each of end-seal assemblies 10, 20 has a forward end, a rear end and a longitudinal axis. The forward end of the receptacle end-seal assembly 10 is mateable with the forward end of the plug end-seal assembly 20 as shown in FIGS. 16-18. The receptacle end-seal assembly 10 includes two resilient seal elements 101 (FIG. 2), 102 (FIGS. 2 and 7), back support 103 (FIG. 5), spring guide-bore 104 (FIG. 5), spring 105 (FIG. 4), and spring retainer ring 106 (FIG. 4). End-seal element 102 is movable within end seal element 101 between a first position (FIGS. 1, 1a and 4) when plug and receptacle units 10, 20 are unmated, to a second position (FIGS. 3, 3a and 6) when the units are mated. Elements 101, 102 of plug end-seal assembly 10 are shown juxtaposed for clarity in FIG. 2. Seal elements 101, back support 103 and spring retainer ring 106 are substantially fixed relative to one another. Spring 105 is free to flex along its axis within spring bore 104. Seal element 102 (FIGS. 2 and 7) is a sub-assembly comprising integral spine 107 and resilient seal element 108. Seal sub-assembly 102 is free to slide laterally within slot 111 (FIGS. 1a, 3a, 4 and 5) of seal element 101, moving against spring 105. Seal elements 101, 102 have raised surfaces 109, 110 (FIGS. 1a, 3a, 4 and 6) respectively. Raised surface 109 is generally "C-shaped" as shown in FIG. 2 and includes interior surfaces 116, 117 and 120 forming an opening 115. Spine 107 includes a central guide portion 112 (1a, 3a and 7) which is similarly free to slide laterally in unison with seal element 108 of seal sub-assembly 102, the two elements 107 and 108 being parts of the integral sub-assembly.

Figure 1A:
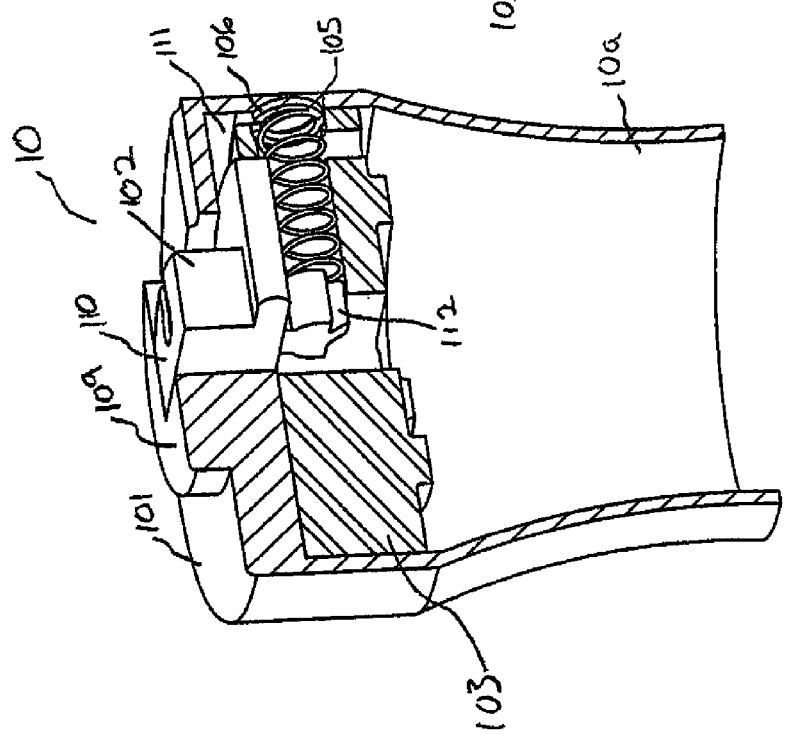
FIG. 1a is a partial cross-sectional perspective view of the receptacle end-seal in the unmated (closed) condition.
Figure 5:
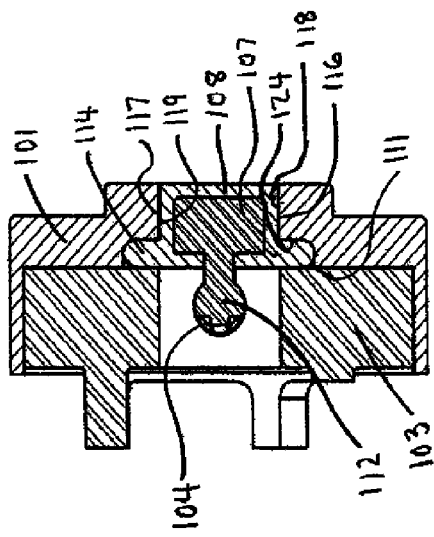
Figure 7:
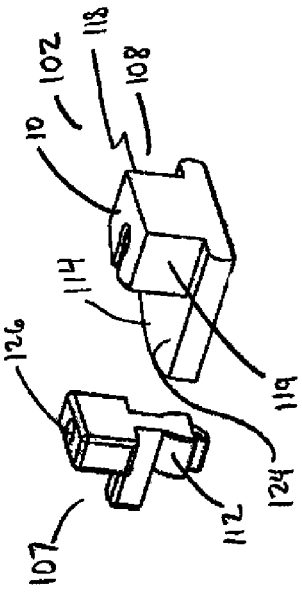

Opening 115 of "C-shaped" raised surface 109 extends axially through seal element 101. Surfaces 116 and 117 of the C-shaped opening sealably fit to corresponding surfaces 118 and 119 (FIGS. 2, 5 and 7) of seal element 108. Surface 120 of seal element 101 conforms to surface 121 (FIG. 2) of seal element 108. Surface 121 is sealably pressed against surface 120 by spring 105 (FIG. 1a) when seal assembly 10 is in the unmated (closed) condition (FIG. 1). Surface 124 (FIG. 7) on wide portion 114 (FIG. 5) of seal element 108 is free to slide sealably along surface 129 (FIGS. 4 and 6) of seal element 101. Portions of the surface 124 remain sealably in contact with surface 129 of slot 111 in seal element 102 at all times. Passage 125 (FIG. 4) through back support 103 ventilates spring bore 104 to the receptacle reservoir 10a of the assembly. Note therefore that spring bore 104 is effectively an extension of the receptacle reservoir 10a.

Plug end-seal assembly 20 (FIGS. 8 through 15) includes two resilient seal elements 201 (FIG. 9), 202 (FIGS. 9 and 15), back support 203 (FIG. 11), spring guide-bore 204 (FIG. 11), spring 205 (FIG. 11), and spring retainer ring 206 (FIG. 11). End-seal assembly 202 is movable within end seal element 201 between a first position (FIG. 8) when plug and receptacle units 10, 20 are unmated, to a second position (FIG. 10) when the units are mated. Elements 201, 202 of plug end-seal assembly 20 are shown juxtaposed for clarity in FIG. 9. Seal elements 201, along with back support 203 and spring retainer ring 206 are substantially fixed relative to one another. Spring 205 (FIGS. 11 and 13) is free to flex along its axis within spring bore 204. Seal element 202 (FIG. 15) is a sub-assembly including an integral spine 207, actuator pin 230 and resilient seal element 208. Ribs 234 on spine 207 reduce friction between spine 207 and bore 204 as the spine slides within the bore. Seal sub-assembly 202 is free to slide laterally within slot 211 of seal element 201, moving against spring 205. Seal elements 201, 202 have raised surfaces 209, 210 (FIG. 9) respectively. Raised surface 209 is generally "C-shaped" as shown in FIG. 9 and includes interior surfaces 216, 217 and 220 forming an opening 215. Portion 214 of resilient seal element 208 of seal element 202 is free to slide laterally within slot 211 of seal element 201. Portion 212 of spine 207 is similarly free to slide within spring bore 204 of back support 203 in unified motion with portion 214 of seal element 201, the two elements 214 and 201 being parts of an integral sub-assembly including actuator pin 230. Actuator pin 230 is fixed into seat 235 of spine 207 (FIG. 15).

Opening 215 (FIG. 9) of "C-shaped" raised surface 209 extends axially through seal element 201. Surfaces 216 and 217 of the C-shaped opening 215 sealably fit to corresponding surfaces 218 and 219 of resilient seal element 208 of seal element 202. Surface 220 of seal element 201 conforms to surface 221 of resilient seal element 208. Surface 221 is sealably pressed against surface 220 by spring 205 when seal assembly 20 is in the unmated (closed) condition (FIG. 11). Surface 224 on wide portion 214 of seal element 208 is free to slide sealably along surface 223 of slot 211 in seal element 201 (FIG. 12). Portions of the surface 224 remain sealably in contact with surface 223 of slot 211 in seal element 201 at all times. Passage 225 through back support 203 ventilates spring bore 204 to the plug reservoir 20a (FIGS. 11 and 16). Note therefore that spring bore 204 is effectively an extension of the plug reservoir 20a.

Tubular plug stem 226 (FIGS. 11-13 and 16-19) of plug seal assembly 20 is fitted on its anterior end with actuator tip 227. Actuator tip 227 has angled faces 228 (FIGS. 14 and 19) that approximately conform to angled face 212 (FIG. 15) of spine 207 in seal sub-assembly 202. Seal element 202 further includes a spring 229 suitably fixed within the posterior portion of the plug reservoir 20a, and surrounding plug stem 226. Except for plug stem 226 with actuator tip 227 and spring 229, the other elements of seal assembly 20 can be forced to move axially inward thereby compressing spring 229. When seal assembly 20 is in the unmated condition (FIG. 11), spring 229 acting against surface 203a of back support 203 keeps the axially movable elements of seal assembly 20 positioned such that actuator tip 227 is just inboard of face 212 of seal sub-assembly 202. Rearward axial force applied to faces 209, 210 of seal assembly 20 causes the axially movable portions of the seal assembly to move inward, compressing spring 229 and causing faces 228 of actuator tip 227 to move against face 212 of seal sub assembly 202. The action causes seal sub-assembly 202 to move laterally outward, much the same as the strike plate on a residential door lock causes the lock's bolt to move aside. As sub-assembly 202 moves laterally outward, spring 205 compresses against spring retainer ring 206. As the movable elements of seal assembly 20 move further axially inward plug stem 226 fully passes beyond faces 209 and 210 of the seal assembly (FIG. 13).

FIGS. 16, 17 and 18 illustrate various stages of the plug and receptacle mating sequence. When plug seal assembly 20 and receptacle seal assembly 10 are mated the two units are first brought into rotational and axial alignment as shown on FIG. 16. The units are next pressed axially together as shown in FIG. 17, the action causing faces 109, 209 and 110, 210 respectively to sealably press against each other, and simultaneously causing actuator pin 230 of plug sub-assembly 202 to fully engage bore 126 of receptacle sub-assembly 102 (FIG. 17). Sub-assemblies 102, 202 are thus locked in such a way that lateral outward movement of one of the sub-assemblies is faithfully tracked by identical lateral outward movement of the other sub-assembly. It is noted that the interface between seal assembly 10 and seal assembly 20 is at this point completely sealed from the outside environment.

With further engagement (FIG. 18), the applied axial force overcomes the pre-load of spring 229. Spring 229 compresses and forces plug and receptacle seal assemblies 10, 20 more tightly together. The increased engagement moves actuator tip 227 of seal assembly 20 against face 212 of spine 207 of sub-assembly 202, thereby moving the sub-assembly laterally outward. As plug sub-assembly 202 moves laterally outward receptacle sub-assembly 102 moves in lock-step with it as a result of the engagement of actuator pin 230 in bore 126. It is noted that as the aforementioned sub-assemblies move laterally outward their opposed faces 110, 210 remain sealed together, and they each remain sealed within their respective end seal assemblies 10, 20. Thus, the interface between plug and receptacle assemblies 10 and 20 remains sealed from the outside environment during the entire mating process. As mating completes, plug stem 226 with actuator tip 227 passes through the resilient elements of plug seal assembly 20, thence through receptacle seal assembly 10 and into the receptacle reservoir 10a. Passages 231 and 232 of plug stem 226 and actuator tip 227 respectively thus form an open channel through plug and receptacle elastomeric end-seals, thereby joining the plug and receptacle reservoirs 20a, 10a.

When the coupler is fully mated, the interface between receptacle and plug assemblies 10, 20 is sealed from the outside environment due to the fact that compressed plug spring 229 firmly presses receptacle faces 109, 110 against respective opposed plug faces 209, 210. The other resilient interfaces in seal assemblies 10, 20 remain sealed at all times. The demating operation is just the reverse of the mating sequence. Therefore, the coupler is sealed from the outside environment before, during, and after mating. In the mated connector, slots 127, 128 (FIGS. 1 and 3) in receptacle end-seal assembly 10 cooperate with slots 236, 237 (FIGS. 8-10) in plug end-seal assembly 20 to ventilate bore 126 of seal sub-assembly 102 which is axially arranged with slot 127 in raised surface 110 of receptacle sub-assembly 102. The slots also ventilate the exposed portion of surface 124 of flexible element 108. Without the slots the small volumes they ventilate would be sealed both from plug reservoir 20a and receptacle reservoir 10a (FIG. 17), and from the ambient in-situ environment. In the case where the in-situ environment is highly pressurized, such as in the deep sea, without such ventilation the small volumes would collapse, possibly damaging the end-seal assemblies and causing failure of the connected units.

In the foregoing discussion there has been no requirement to achieve a seal to plug stem 226. Note, however, that receptacle and plug shuttle springs 105, 205 urge faces 121, 221 of seal sub-assemblies 102, 202 respectively against face 233 (FIG. 19) of plug stem 226. Face 233 of plug stem 226 may be configured to conform to faces 121, 221, and the other faces of plug stem 226 may be configured to conform to their respective other elastomeric faces of openings 115, 215, and plug stem 226 may be sized to have a slight interference fit to the resilient faces; such that a second level of sealing is achieved between the mated plug and receptacle reservoirs 20a, 10a and the outside environment. Such a second sealing barrier is often a reliability requirement.

The second coupler embodiment (FIGS. 20-25) will be easily understood from the foregoing description of the first embodiment and the following discussion. The primary difference between the two embodiments is that the second embodiment employs two radially opposed sliding seal sub-assemblies instead of only one. The second embodiment can be somewhat more compact; it requires that in order to form the same size opening through the mated end seals each second-embodiment seal sub-assembly has to move only half the lateral distance as does the single seal sub-assembly of the first embodiment. However, the second embodiment has more parts; and it is more complicated. Choice of the first or second embodiment therefore depends on the particular application.

FIG. 20 is a mating-face view of the second-embodiment receptacle end-seal in the unmated (closed) condition. This second-described embodiment of the invention employs two movable sliding-seal sub-assemblies in each of the plug and receptacle units (FIGS. 21-23). Receptacle end-seal assembly 30 includes three resilient seal elements 301, 302a, 302b; back support 303 (FIG. 22), spring guide-bores 304a, 304b; springs 305a, 305b, and spring retainer rings 306a, 306b. Seal element 301 along with back support 303 and spring retainer rings 306a, 306b are substantially fixed relative to one another. Springs 305a, 305b are free to flex along their axes within respective spring bores 304a, 304b. Seal elements 302a and 302b (FIG. 20) are sub-assemblies which are for all practical purposes identical to sub-assemblies 102 of the first-described coupler embodiment. Seal element 301 has raised surfaces 309a, 309b (FIG. 20). Seal sub-assemblies 302a, 302b are free to slide laterally within their respective slotted seats in element 301 in just the same way that sub-assembly 102 was free to slide within its slotted seat in seal element 101 of the previously described first embodiment of the receptacle seal assembly.

Plug end-seal assembly 40 (FIGS. 23-25) includes three resilient seal elements 401, 402a, 402b; back support 403 (FIG. 24); spring guide-bores 404a, 404b; springs 405a, 405b; and spring retainer rings 406a, 406b. Seal element 401 along with back support 403 and spring retainer rings 406a, 406b are substantially fixed relative to one another. Springs 405a, 405b are free to flex along their axes within respective spring bores 404a, 404b. Seal elements 402a and 402b (FIG. 23) are sub-assemblies which are for all practical purposes identical to sub-assembly 202 of the first described embodiment. Seal element 401 has raised surfaces 409a, 409b. Seal elements 402a and 402b have raised surfaces 410a, 410b respectively. Seal sub-assemblies 402a, 402b are free to slide radially within their respective slotted seats in element 401 in just the same way that sub-assembly 202 was free to slide within its slotted seat in seal element 201 of the previously described first embodiment of the plug seal assembly.

Tubular stem 426 (FIG. 24) of plug seal assembly 40 is fitted on its anterior end with actuator tip 427. Actuator tip 427 (FIG. 25) has angled faces 428a, 428b that approximately conform to angled faces 412a, 412b of seal sub-assemblies 402a, and 402b respectively. Except for plug stem 426 with actuator tip 427 and spring 429, the other elements of seal assembly 40 can be forced to move axially inward thereby compressing spring 429. When seal assembly 40 is in the unmated condition, spring 429 acting against surface 431 of back support 403 keeps the axially-movable elements of seal assembly 40 positioned such that actuator tip 427 is just inboard of angled faces 412a, 412b of seal sub-assemblies 402a, and 402b respectively. A rearward axial force applied to faces 409a, 409b and 410a, 410b of seal assembly 40 causes the axially movable portions of seal assembly 40 to move inward, compressing spring 429 and causing faces 428a, 428b of actuator tip 427 to move against faces 412a, 412b of seal sub-assemblies 402a, and 402b respectively. The action causes sub-assemblies 402a, and 402b to move laterally outward, in a manner identical to the similar movement of sub-assembly 202 of the previously described first embodiment of the invention. As sub-assemblies 402a, and 402b move laterally outward, springs 405a, 405b compress against respective spring retainer rings 406a, 406b. As the movable elements of seal assembly 40 move further axially inward plug stem 426 fully passes beyond faces 409a, 409b and 410a, 410b of the seal assembly (FIG. 24).

In the preceding discussion of the second embodiment of the invention there has again been no requirement to achieve a seal to plug stem 426. Note that, similar to the first embodiment, when the exterior faces of plug stem 426 is configured to conform to the respective resilient faces of openings 315, 415, and when plug stem 426 is sized to have a slight interference fit to the resilient faces, a second level of sealing is achieved between the mated plug and receptacle reservoirs and the outside environment just as it was for the first embodiment.

There are many harsh-environment applications that require electrical connections and/or some combination of electrical and fiber-optical connections to be housed within the same connector units. FIGS. 26 through 50 illustrate a third embodiment of the coupling mechanism configured for use as an electrical, optical, or hybrid electro-optical connector, and having a single sliding end-seal assembly in each of the plug and receptacle. Alternatively, the connector depicted in FIGS. 26 through 38 may also be reconfigured with two radially opposed sliding seal sub-assemblies as described above with respect to FIGS. 20 through 25. Note that in the embodiment next described, the contact assemblies are not arranged along the plug and receptacle center axes as in the previous embodiment, but rather are displaced to one side to conserve radial space.

The third-described coupler embodiment, shown in FIGS. 26 through 50, illustrates a connector suitable for various harsh environment applications including subsea telecommunications, submarine systems, underwater oil and gas systems, etc. The connector may also be used in many other harsh applications due to the fact that the optical and electrical contacts remain sealed from the outside environment at all times including before, during and after mating of the receptacle unit 500 and the plug unit 600. In the illustrated embodiment, the receptacle unit 500 and the plug unit 600 each carry electrical and/or optical contacts. Specifically, the plug unit 600 houses a first one or a plurality of contact junctions within a first chamber sealed from the external environment. The receptacle unit 500 houses a respective second one or a plurality of contact junctions within a second chamber sealed from the external environment. When the plug and receptacle units 600, 500 are mated, the first and second chambers are sealably joined together, thereby joining the respective first one or a plurality of contact junctions to a respective second one or a plurality of contact junctions. When the units 600, 500 are subsequently demated the first and second chambers are once again separately sealed from the operating environment. The contact junctions can join, for example, the conductors of various subsea electrical and/or fiber optical cables.

Figure 29:
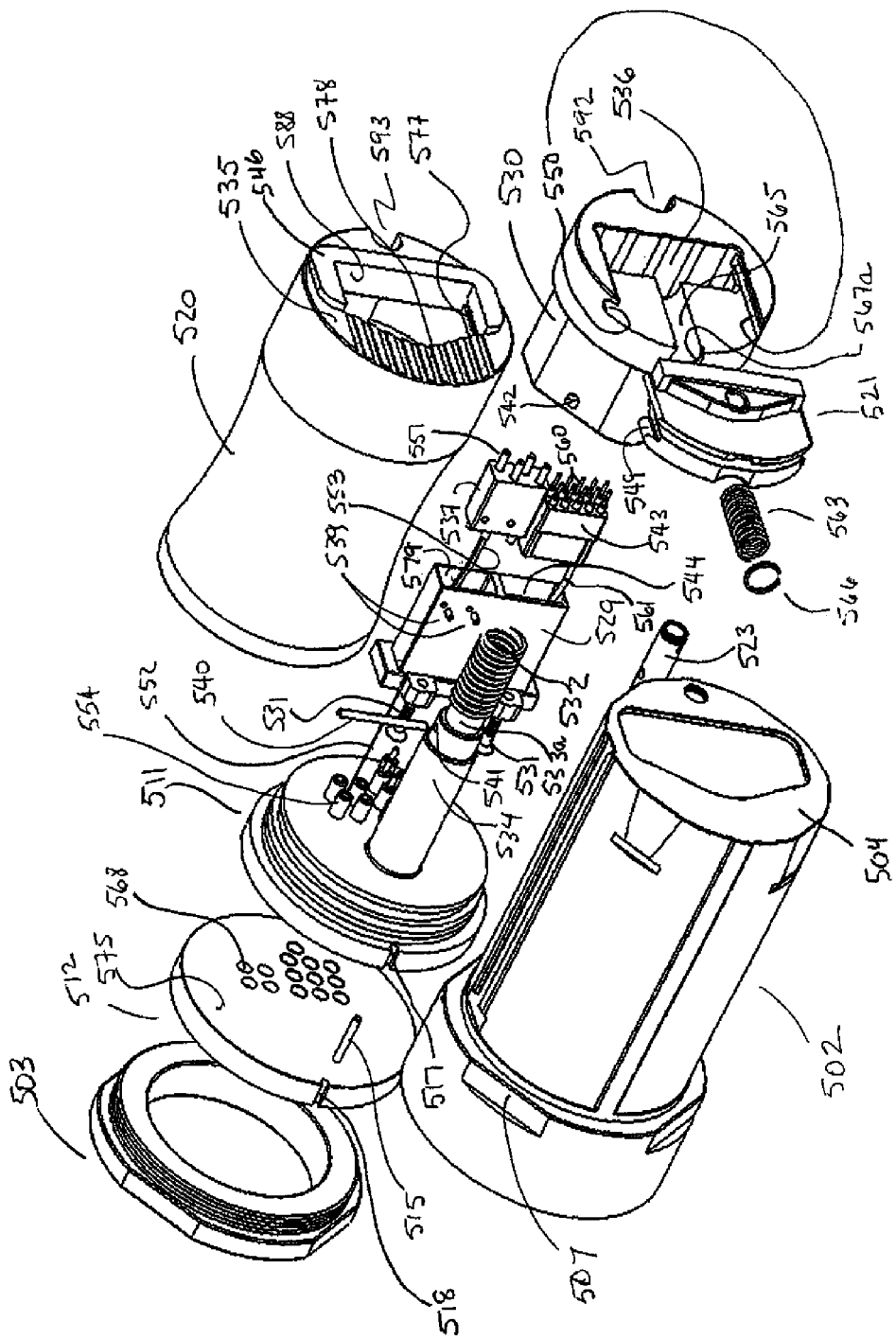
Figure 33:
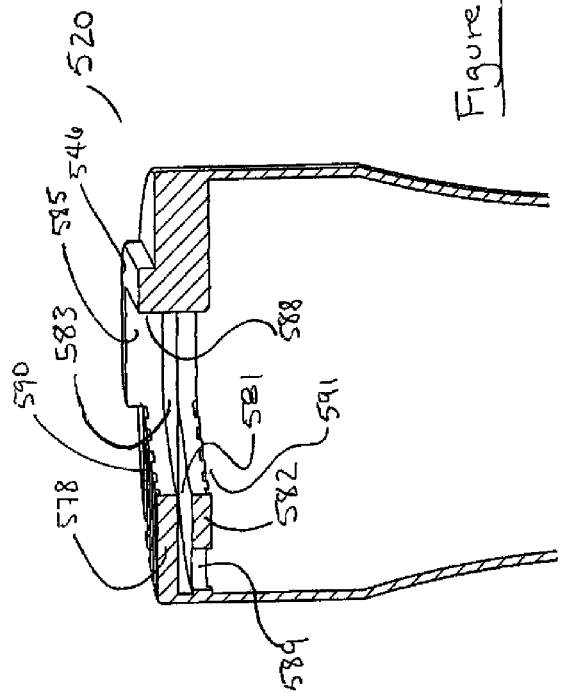
Figure 35:
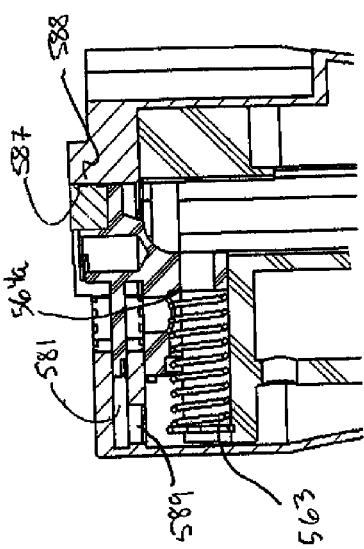
Figure 34:
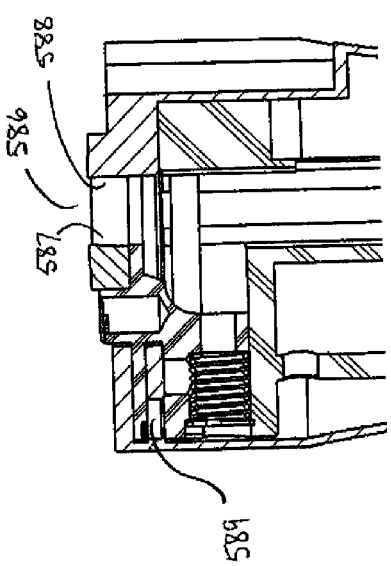

The structure of receptacle unit 500 is shown in FIGS. 26 through 35. For clarity, in FIG. 26 receptacle front shell 502, resilient bladder 520, and back-up block 530 are shown cutaway in axial half-section. FIG. 29 shows the receptacle components in exploded view. Receptacle front shell 502 cooperates with receptacle rear nut 503 to form the outer rigid portion of unit 500. Wrench flats 507 (FIG. 29) of receptacle front shell 502 and wrench flats 508 (FIG. 26) of receptacle rear nut 503 aid to tighten threaded junction 538 between front shell 502 and rear nut 503. Front end 504 of receptacle shell 502 arrests the forward axial motion of the internal portions of unit 500, while rear nut 503 arrests the rearward motion of the inner portions. Shoulder 510 of receptacle base 511, and back plate 512 are axially captured between face 513 of rear nut 503 and face 514 of front shell 502. Alignment pin 515 (FIG. 29) is housed in bore 516 (FIG. 26) of front shell 502, and resides in slot 517 of shoulder 510 of receptacle base 511 and in slot 518 of back plate 512 thereby rotationally locking receptacle base 511 and back plate 512 to front shell 502. Reservoir 519 (FIG. 26) is defined by resilient bladder 520 with rear sealing shoulder 528, receptacle base 511 with o-ring seal 527, and end-seal assembly 521. Reservoir 519 is filled with a benign mobile substance 522 (hereafter called a "fluid" for brevity). Fluid 522 is typically chosen to have an optical index of refraction which closely matches that of the optical fibers (if any) to be connected, to be substantially non-conductive electrically, and to be chemically compatible with the other elements of the connector unit with which it comes in contact. Fluid 522, for example, may be a dielectric substance such as an oil. Vent tube 523 is open to the operating environment through port 524. Radial ports 525 in vent tube 523 communicate the external environment to annular space 526 formed between receptacle shell 502 and flexible chamber wall 520a of bladder 520, thereby balancing the pressure of fluid 522 within chamber 519 to that of the outside environment. Vent tube 523 is rigidly fixed to front end 504 of receptacle shell 502. Back-up block 530 is rotationally aligned by engagement with axially-offset standoff 534 which projects forward from receptacle base 511. Tolerances of the engagement between back-up block 530 and standoff 534 are chosen so as to permit a controlled compliance of axial tilt and offset between said back-up block and said standoff. Bladder 520 is maintained in a substantially compliant rotational alignment within shell 502 by trapping vent-tube seat 593 between vent tube 523 and cut-out 592 of back-up block 530.

Referring to FIG. 29, contact housing 529 is mounted to back-up block 530 by screws 531. Receptacle mainspring 532 seats to extension 533a of standoff 534 of receptacle base 511, and is guided by bore 533b of back-up block 530. Receptacle mainspring 532 serves to urge back-up block 530 against front wall 535 of resilient bladder 520, thereby squeezing front wall 535 between back-up block 530 and front end 504 of receptacle shell 502, thus serving to guarantee the forward axial position of C-shaped projection 546 of front wall 535. C-shaped projection 546 forms the fixed portion of the receptacle end-seal. End-seal assembly 521 shown in FIGS. 27 and 28 is the laterally-sliding portion of the receptacle end seal is the equivalent to receptacle end seal 102 of the previously described first embodiment of the plug seal assembly. The end-seal assembly 521 includes a rigid seal-mount 547 (FIG. 28) and resilient seal 548. Resilient seal 548 is affixed to seal mount 547 by adhesive bond or by other standard means. Raised ribs 549 on seal mount 547 fit slidably into slots 550 of back-up block 530, thereby permitting end-seal assembly 521 to accurately slide laterally within back-up block 530. Receptacle shuttle spring 563 acts against portion 564a (FIG. 35) of seal mount 547, thereby urging end seal assembly 521 laterally inward. Shuttle spring 563 is retained in partially-open bore 565 of back-up block 530 by retainer ring 566, the ring being seated in groove 567a of back-up block 530.

Contact housing 529 is slidably fitted within through-port 536 (FIG. 29) of back-up block 530. Optical contact-block 537 seats within rectangular socket 579 of contact housing 529 and is fixed to the contact housing 529 by pressed-in pins 539 or by other standard means. Pin 540 shown in FIG. 29 is an assembly aid. It passes through opposed, axially-elongated, slots 542 in back-up block 530; and is press-fit or otherwise fixed in bore 541 of receptacle base 511, thereby limiting the axial movement between receptacle base 511 and the back-up block 530 during assembly. One or a plurality of optical contact assemblies 551 are suitably mounted in optical contact block 537 and are terminated to a respective one or a plurality of optical fibers 552 which may be routed through respective furcation tubes 553 thence through respective optical penetrators 554 (one example is shown in FIG. 30 and in axial cross-section in FIG. 31). Typical optical penetrator 554 comprises rigid body 555, o-rings 556 and shaped throughbore 557. A typical optical fiber is sealably affixed with epoxy or another suitable adhesive sealant within bore 557 by standard means. One end of typical elastomeric sleeve 558 (FIG. 26) fits snugly over nipple 559 of typical optical penetrator 554. The other end of typical elastomeric sleeve 558 fits snugly to typical respective furcation tube 553.

Electrical contact-block 543 (FIG. 29) seats within rectangular socket 544 of contact housing 529 and is fixed to contact housing 529 by an adhesive or by other standard means. One or a plurality of electrical contacts 560 are suitably mounted in electrical contact block 543 and are terminated to a respective one or a plurality of insulated electrical conductors 561 sized to fit sealably into respective contact-block bores 561a (FIG. 47). Conductors 561 are routed to respective electrical penetrators 562 (one example is shown in FIG. 30 and in axial cross-section in FIG. 32). Typical electrical penetrator 562 comprises rigid body 563, o-rings 564, and electrical conductor 566a with a solder pot 566 or other termination means on either end. One end of typical elastomeric sleeve 558 fits sealably over nipple 569 of typical electrical penetrator 562. The other end of typical elastomeric sleeve 558 fits sealably to the insulating jacket of typical electrical conductors 561. Each optical penetrator 554 (FIG. 31) and each electrical penetrator 562 (FIG. 32) is housed in a respective bore 567 (FIG. 30) in receptacle base 511. Bore 567 has a posterior diameter sized to seal against typical optical penetrator o-rings 556 (FIG. 31) or electrical penetrator o-rings 564 (FIG. 32), and a smaller anterior diameter 568 (FIG. 26), sized to fit snugly to optical penetrator nipple 559 or electrical penetrator nipple 569. Optical penetrators 554 and electrical penetrators 562 are loaded into bores 567 in receptacle seat 511 from the rear. Shoulders 569 and 570 on optical penetrators 554 and electrical penetrators 562, respectively, limit the forward travel of the penetrators within bores 567. Bores 568 (FIG. 29) in back-plate 512 are sized to fit snugly to optical penetrator nipple 571 or electrical penetrator nipple 572. Shoulders 573 and 574 on optical penetrators 554 and electrical penetrators 562, respectively, reacting against face 575 of back plate 512 limit the rearward travel of the penetrators within bores 567.

Tabular portion 580 (FIG. 27) of end-seal assembly 521 fits snugly within slot 581 (FIG. 33) of resilient receptacle bladder 520. Receptacle mainspring 532 acting with back-up block 530 insures that tabular portion 580 is sealably squeezed between end wall 578 and inner wall 582 of bladder 520. Furthermore, opposed side lobes 576 of tabular portion 580 stretch-fit laterally into side slots 583 of slot 581, thereby sealing to the side slots. End portions 584 (FIG. 28) of resilient seal 548 sealably press to side walls 585 of raised C-shaped projection 546 of bladder 520. Receptacle end-seal assembly 521 is free to move laterally between an outward position, as shown in FIG. 26 and full axial cross-section in FIG. 34, in which an opening 586 exists in the anterior end of receptacle 500 and an inward position, as shown in full axial cross-section in FIG. 35, in which the anterior end of the receptacle is closed and sealed. When receptacle 500 is closed, in addition to the aforementioned seals, face 587 of resilient seal 548 (FIG. 28) is pressed tightly by shuttle spring 563 (FIG. 29) against resilient face 588 of C-shaped projection 546 of bladder 520 (FIG. 33), thereby sealing that interface. As end-seal assembly 521 slides sealably between its inward and outward positions, fluid 522 is exchanged through port 589 in bladder 520 to prevent hydraulic locking of tab 580 within slot 581. Ribs 590 and 591 (FIG. 33) on portions of end-walls 578, 582 of bladder 520 allow the end-wall portions to be firmly squeezed axially by receptacle mainspring 532 while still facilitating resilient deformation of the end-walls, thereby improving the conformation of the end-wall portion to tabular portion 580 of end-seal assembly 521.

Figure 39:
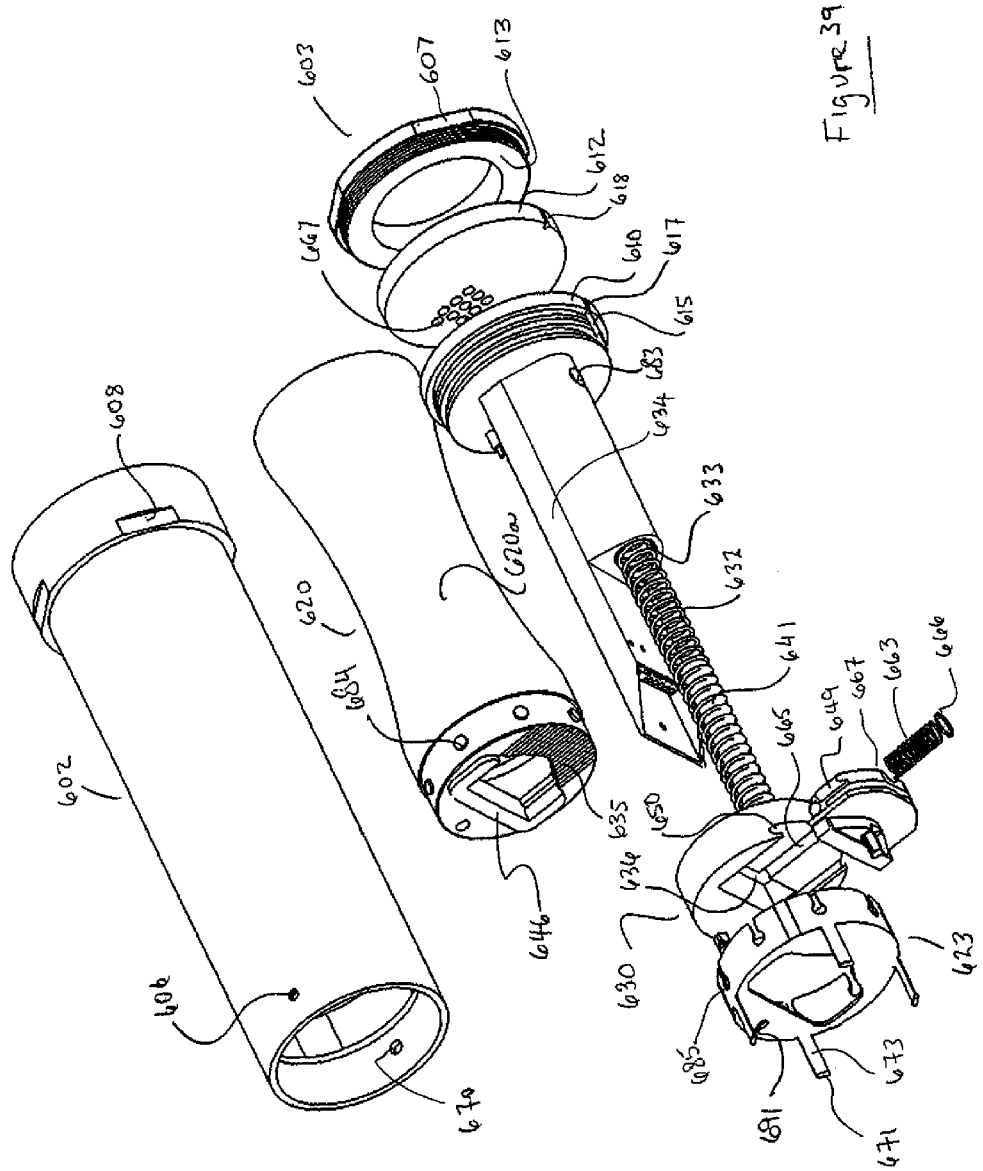

The structure of plug unit 600 is shown in FIGS. 36 through 42b. For clarity, in FIG. 36 plug front shell 602, resilient bladder 620 and back-up block 630 are shown cut-away in axial half-section. FIG. 39 shows the plug components in exploded view. Plug front shell 602 cooperates with plug rear nut 603 and plug end-cap 623 to form the outer rigid portion of unit 600. Wrench flats 608 (FIG. 39) of plug front shell 602 and wrench flats 607 (FIG. 36) of plug rear nut 603 aid to tighten threaded junction 638 between front shell 602 and rear nut 603. Small shoulder 604 of plug shell 602 arrests the forward axial motion of end-cap 623, and thereby arrests the forward axial motion of plug anterior assembly 701 (FIGS. 41a and 42a), while rear nut 603 arrests the rearward motion plug base 611. In the unmated condition, plug anterior assembly 701, is urged forward against shoulder 604 by plug mainspring 632. Shoulder 610 of plug base 611 and back plate 612 are axially captured between face 613 of rear nut 603 and shoulder 614 of plug shell 602. Alignment pin 615 is housed in bore 616 of plug shell 602, and resides in slot 617 of shoulder 610 of plug base 611 and in slot 618 of back plate 612, thereby rotationally locking plug base 611 and back plate 612 to plug shell 602. Reservoir 619 is defined by resilient bladder 620 with outer wall 620a and front wall 635; rear sealing shoulder 628; plug base 610 with o-ring seal 627; and end-seal assembly 621. Reservoir 619 is filled with a benign mobile substance 522 (plug and receptacle fluids are typically the same). Radial space 625 between inner wall 676 of plug shell 602 and the outer radial wall 620a of bladder 620 communicates to the external environment medium via annular space 626 formed between plug shell 602 and plug end-cap 623, thereby balancing the pressure of fluid 522 within chamber 619 to that of the outside environment.

Plug mainspring 632 (FIG. 39) seats in spring bore 633 of plug stem 634, the stem projecting into chamber 619 from plug base 611, and is guided by post 641 of back-up block 630. Spring bore 633 of plug base 611 is ventilated by port 683 (FIG. 40) in the base of plug stem 634 to prevent hydraulic resistance against guide post 641 during mating. Plug mainspring 632 serves to urge back-up block 630 against front wall 635 (FIG. 36) of resilient bladder 620, thereby squeezing front wall 635 between the back-up block and the inner surface of end-cap 623; thus serving to guarantee the forward axial position of C-shaped projection 646 (FIG. 39) of front wall 635 with respect to end-cap 623, and further assuring that the end-cap and bladder front-wall 635 are simultaneously urged axially in the forward direction. C-shaped projection 646 forms the fixed portion of the plug end-seal. End-seal assembly 621 shown in FIGS. 37 and 38 is the lateral-sliding portion of the plug end seal. The end-seal assembly includes a rigid seal mount 647, actuator pin 629, rod 631, and resilient seal 648. Seal 648 is affixed to seal mount 647 by adhesive bond or by other standard means. Rod 631 is free to rotate within partial bore 652 in seal mount 647. Rod 631 serves to reduce friction between tapered plug tip 681 and end-seal assembly 621 during mating (FIG. 42a). Raised ribs 649 on seal mount 647 fit slidably into slots 650 (FIG. 39) of back-up block 630, thereby permitting end-seal assembly 621 to accurately slide laterally within the back-up block. Plug shuttle spring 663 acts against the rear surface of portion 664 of seal mount 647, thereby urging seal assembly 621 laterally inward. Shuttle spring 663 is retained in partially-open bore 665 of back-up block 630 by retainer ring 666, the ring being seated in groove 667 of back-up block 630.

The rectangular exterior of the anterior portion of plug stem 634 is slidably engaged axially within rectangular through-port 636 (FIG. 39) of back-up block 630. Tolerances between the respective, engaged, rectangular features are chosen to permit a controlled amount compliance in axial tilt, offset, and rotational alignment between the stem and back-up block. Engagement pin 651 (FIG. 36) is rigidly fixed to plug end-cap 623. Inward projection 653 of engagement pin 651 fits into socket 654 of bladder anterior wall 635 aiding the rotational alignment of the end-cap to bladder 620. Optical contact-block 637 (FIG. 40) is fixed within the open anterior portion of plug stem 634 by set screws 639 or by other standard means. Electrical contact-block 643 is fixed by an adhesive or by other standard means within the open anterior portion of stem 634. The plug optical and electrical penetrators and the routing of optical and electrical conductors within the plug are identical to those of the receptacle described earlier. The mounting of optical and electrical penetrators, 561, 562 within plug 600 are likewise identical the manner in which they are mounted in receptacle 500. For brevity, the description is not repeated here. The plug and receptacle end-seal assemblies, 521, 621 respectively, are only slightly different from each other, as are the anterior portions of respective bladders 520, 620. Therefore, a comprehensive understanding of the sealing between plug end-seal assembly 621 and plug bladder 620 is easily gained by a study of FIGS. 33, 34 and 35 and their accompanying descriptions.

Plug anterior assembly 701 (FIGS. 41a and 42a) includes a forward portion 635 (FIG. 39) of bladder 620; back-up block 630; end-cap 623; end-seal assembly 621; shuttle spring 663; retainer ring 666; and engagement pin 651. Anterior assembly 701 is maintained in compliant rotational and axially alignment with actuator stem 634 by the fit tolerances of rectangular plug actuator stem 634 within rectangular through port 636 of back-up block 630. Nibs 684 (FIGS. 39 and 42a) of bladder 620 protrude radially outward through holes 685 (FIG. 39) in end-cap 623 allowing compliant radial retention of anterior assembly 701 within plug shell 602. Anterior assembly 701 is axially slidable as a monolithic unit within plug shell 602 between a forward position as shown in FIG. 41a, and a rearward position as shown in FIG. 42a. Nibs 684 ride against inner wall 676 of plug shell 602, keeping anterior assembly 701 approximately radially centered as it moves from a forward to a rearward position. Nibs 684 also serve to minimize friction and galling as might occur if the contact between adjacent sliding surfaces within the plug were metal-to-metal, and permit some compliance in the fit of anterior assembly 701 within plug shell 602. When the plug anterior assembly is in the forward position as shown in FIG. 41a, end-seal assembly 621 is closed (FIG. 41b), as it would be when the connector plug and receptacle units are not mated, and end-seal 648 is pressed tightly against raised C-shaped fixed end-seal projection 646. When plug anterior assembly 701 is in the rearward position as shown in FIG. 42a, end-seal assembly 621 is open (FIG. 42b), as it would be when the connector plug and receptacle units are mated.

Plug unit 600 and receptacle unit 500 are shown unmated in FIGS. 43 and 44; and shown mated in FIG. 45. Mating of receptacle unit 500 and plug unit 600 is as follows. Raised axial ribs 505 spaced radially at intervals on the outer surface of receptacle front shell 502 fit closely to raised lands 605 on inner wall 676 of plug shell 600, thereby axially aligning the receptacle and plug shells when the units are mated (FIGS. 43 and 44). Keyway 506 formed between two of ribs 505 of receptacle front shell 502 cooperate with inward projecting key 606 of plug front shell 602 to rotationally align plug front shell 602 and receptacle front shell 502 as mating of the plug and receptacle proceeds. Equalization of pressure between the outside environment and the interior portions of the plug and receptacle units is achieved as follows. Smaller diameter portions 509 between ribs 505 of receptacle shell 502 aligned with corresponding larger diameter plug-shell portions between lands 605 on inner wall 676 provide free ventilation paths between the inner wall 676 of plug shell 602 and the outside of receptacle front shell 502 during and after the mating of plug 600 and receptacle 500. During mating, as anterior assembly 701 moves from its forward position to its rearward position bladder 620 is foreshortened axially. Bladder wall 620a is designed so that chamber 619 remains of substantially constant volume during the foreshortening, the constant volume being maintained by a net outward expansion of outer wall 620a. That means the volume of space 625 (FIGS. 41a and 42a) between outer wall 620a of bladder 620 and inner wall 676 of plug shell 602 proportionately diminishes as anterior assembly 701 moves toward its rearward position, thereby expelling the material displaced from space 625 externally through the aforementioned ventilation paths. Assembly port 670 (FIG. 44) in plug shell 602 allows easy access for the assembly of inward projecting alignment key 606 (FIG. 45), and further permits a ventilation path from the outside environment to the space between receptacle shell 502 and plug shell 602 when the units are fully mated. As mating proceeds, axially and rotationally aligned receptacle 500 enters plug shell 602 until shaped ends 671 (FIGS. 41a and 42a) of outwardly-projecting tines 673 of plug end-cap 623 encounter tapered ramps 594 (FIG. 43) of receptacle shell 502. The ramps 594 spring the tines outward, trapping shaped ends 671 (FIGS. 41a and 42a) in groove 674 of plug shell 602, and thereby temporarily arresting any possible inward movement of plug anterior assembly 701. Receptacle 500 enters plug 600 further, and engagement pin 651 (FIGS. 41a and 42a) enters port 524 (FIG. 26) of vent tube 523, thereby locking the rotational and lateral alignment of anterior assembly 701 and receptacle 500. Flats 677 on engagement pin 651 provide ventilation around the pin into bore 524 of vent tube 523. Slot 691 (FIG. 42b) on the front face of plug end-cap 623 leads from the outer diameter of the end cap to the base of engagement pin 651 thereby ventilating socket 524 of receptacle vent tube 523 when the connector plug and receptacle units are fully mated. Plug actuator pin 629 enters actuator socket 595 of receptacle end-seal assembly 521. Flats 678 on actuator pin 629 provide ventilation around the pin into actuator socket 595 of receptacle sliding seal assembly 621. Further receptacle and plug engagement presses together axially-resilient C-shaped projections 546, 646 of receptacle and plug units, respectively, and simultaneously presses together anterior face 596b of receptacle resilient end seal 548 against anterior face 675 (FIG. 38) of plug resilient end seal 648 (FIG. 41b), thereby completely sealing the interface between plug chamber 619 and receptacle chamber 519 from the outside environment. Slots 596 (FIG. 27) in receptacle end seal assembly 521 and slots 679 (FIG. 38) of plug sliding end-seal assembly 621 are axially opposed to provide a ventilation path into socket 595 of sliding end-seal assembly 521 when the sliding end-seal assemblies are pressed against each other. At a point in the continued insertion of receptacle 500 into plug 600 where the face-to-face pressure between the aforementioned end-seals reaches a value determined by the pre-load axial force developed by plug mainspring 632, shaped ends 671 (FIGS. 41a and 42a) of outwardly-projecting tines 673 of plug end-cap 623 spring inward into slots 597 (FIG. 43) of receptacle shell 502, freeing them from groove 674 of plug shell 602, and thereby permitting further inward motion of plug anterior-seal assembly 701.

As the mating sequence proceeds, plug anterior-seal assembly 701 (FIG. 42a) is forced inward by entering receptacle 500, forcing roller 631 of plug end-seal assembly 621 against tapered tip 681 of plug actuator stem 634. Further impalement of the receptacle on actuator stem 634 simultaneously pushes receptacle end-seal assembly 521, and plug end-seal assembly 621 laterally outward, the end-seal assemblies being locked together by actuator pin 629 and actuator socket 595. As mating completes, plug anterior assembly 701 moves from an outward position (FIG. 41a) to an inward position (FIG. 42a) and end-seal assembly 621 moves from a closed position (FIG. 41b) to an open position (FIG. 42b). Depending on the application, it may be desirable to maintain one or more open passages such as 644 (FIG. 42b) between receptacle chamber 519 (FIG. 26) and plug chamber 619 (FIG. 38) when receptacle and plug units 500, 600 are mated. If there is some pumping of fluid between the chambers during mating or demating the chamber volumes can exchange fluid through the open passages to equalize any net fluid exchange. As previously stated plug bladder wall 620a changes shape to maintain a substantially constant volume of chamber 619 during the foreshortening of the chamber as anterior assembly 701 moves between its forward and rearward positions. Receptacle chamber 519 is also maintained at nearly constant volume during mating by the distortion of chamber wall 520a and the concomitant expelling of a relatively small amount of material from space 526 through the ventilation path provided by vent tube 523.

Figure 46:
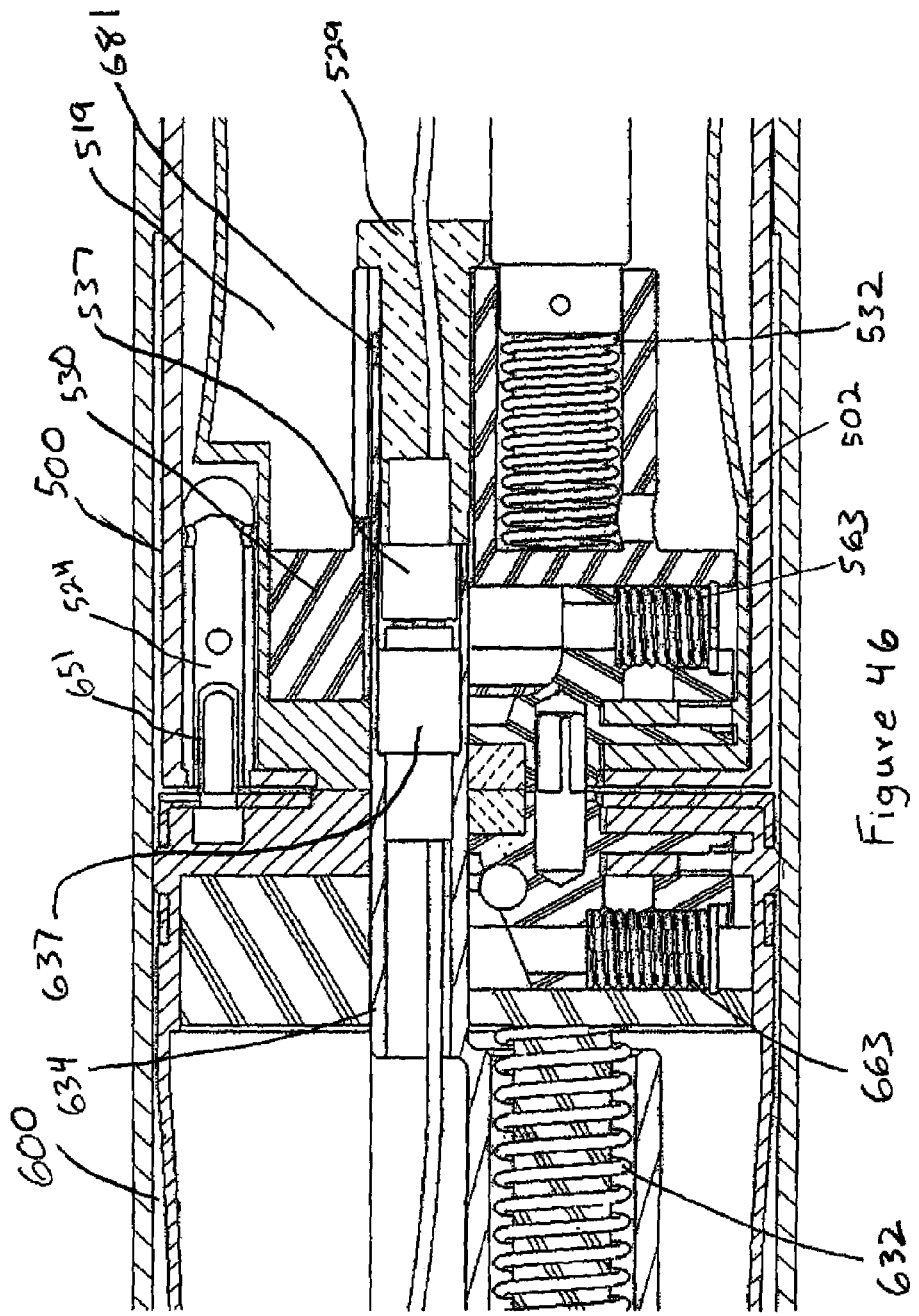

A partial axial cross-section of mated plug and receptacle units 600, 500 is shown in FIG. 46. Hollow tapered tip 681 of plug stem 634 penetrates receptacle chamber 519 capturing receptacle contact housing 529 within conformal cavity 682 (FIG. 40) of plug stem 634, and simultaneously engaging receptacle optical and electrical contact blocks 551, 543 (FIG. 29) with respective plug contact blocks 637, 643 (FIG. 40).

The rotational and axial alignment sequence leading to successful engagement of electrical and optical plug and receptacle contacts is as follows with reference to FIGS. 43-45. First, the exterior plug and receptacle shells (602, 502) are aligned by way of the close fit between the exterior of receptacle shell 502 and raised lands 605 within the bore of plug shell 602, and by way of inward projecting alignment key 606 acting in alignment slot 506. Next, the mating faces of the plug and receptacle end assemblies are further aligned by plug engagement pin 651 engaging within receptacle port 524. Compliance of plug anterior assembly 701 within plug shell 602 permits anterior assembly 701 to move into alignment (FIGS. 41a and 42a). That is followed by the engagement of plug actuator stem 634 within through-port 536 of receptacle back-up block 530 (FIG. 46). The compliant mounting of back-up block 530 within receptacle shell 502 permits back-up block 530, as well as the components fixed to it, to move into alignment with plug actuator stem 634. The next alignment step occurs when receptacle contact housing 529 enters conformal cavity 682 (FIG. 40) in the anterior portion of plug actuator stem 634. The compliance of back-up block 530 with attached contact housing 529 permits sufficient movement to allow the alignment to take place. The final alignment of electrical and optical contacts is possible by way of the compliant mounting of these elements within their respective contact blocks (543, 643 and 537, 637 shown in FIGS. 26 and 40).

FIGS. 47 and 48 illustrate axial cross-sections of plug and receptacle electrical contact blocks 643, 543 in the unmated and mated conditions, respectively. One or a plurality of receptacle electrical contacts 560 reside in resilient contact block 543, contact block 543 having a forward-projecting nib 598 around the pin portion 599 of each one or a plurality of electrical contacts 560. One or a plurality of plug electrical contacts 660 reside in resilient contact block 637, contact block 637 having a forward projecting bore 698 forward of the socket portion 699 of each one or a plurality of electrical contacts 660. Bores 698 may have tapered entrances 622 to facilitate receiving receptacle contact nibs 598 during mating. When fully mated, nibs 598 fit sealably within respective bores 698, trapping a small volume of fluid 522 within bores 698. Nib-and-bore seals of the type just described are known to have been used in underwater connectors as primary seals around pin-socket junctions, permitting such connectors to mate underwater. When used as primary seals, a small amount of water is trapped in each bore surrounding each junction, rendering such connectors somewhat unreliable and short lived. In the third embodiment of the invention, the nib-and-bore seals are engaged within benign fluid 522, trapping a small amount of fluid 522 within bores 698, thereby making them highly reliable and long lived. Also, in this third embodiment of the invention, the nib-and-bore seals are back-up seals, not the primary seals.

FIG. 49 illustrates an axial cross-section of plug and receptacle optical contact assemblies 637, 537 in the mated condition. One or a plurality of plug optical contact assemblies 642 reside in contact block 643. Exploded views of typical plug and receptacle optical contact assembly 642, 551 are shown in FIG. 50. Contact assembly 642 comprises optical junction 645a, optical junction alignment ferrule 655, junction seat 704a, ferrule alignment sleeve 709, back-up washers 705, glide washer 706, compression spring 707a, and retainer ring 708. Sleeve 709 is press-fit or otherwise fixed into the anterior portion of contact-block bore 710. The remaining components of assembly 642 are loaded in to the rear opening of bore 710, and are retained in place by retainer ring 708. To maximize the performance of the optical connection, it is desirable to rotationally align optical junction 645a within contact block 643. That is particularly important when using angle-polished junctions. There are many ways to achieve that rotational alignment. In the illustrated embodiment of the invention there is an inward projecting dimple 711 in ferrule alignment sleeve 709. Dimple 711 projects into alignment slot 712a of ferrule seat 704a, thereby fixing the rotational alignment of ferrule seat 704a to sleeve 709. Sleeve 709 can be rotated within bore 710 of contact block 643 by overcoming the press fit that keeps it in place. That allows individual contact assemblies to be rotationally "tuned" for peak performance within overall assembly 643. Washers 705 sandwich glide washer 706 between them. When the plug and receptacle units 600, 500 are mated springs 707a and 707b are slightly compressed. During compression, the axial faces of springs 707a and 707b tend to rotate around their axes. Glide washers 706 diminish the propagation of that rotation to the optical ferrules.

Receptacle ferrule alignment-sleeve 713 of typical receptacle optical-contact assembly 551 is shorter than comparable alignment sleeve 709 assembly 642, but serves the same purpose. Dimple 714 projects into alignment slot 712b of ferrule seat 704b, thereby fixing the rotational alignment of ferrule seat 704b to sleeve 713. Sleeve 713 is lightly press-fit into bore 715 of contact block 543. Shoulder 716 located at the anterior end of bore 715 arrests the forward motion of sleeve 713 within bore 715. Sleeve 713 can be rotated within bore 715 of contact block 543 by overcoming the slight press fit that keeps it in place. That allows individual contact assemblies to be rotationally "tuned" for peak performance within overall assembly 543. Assembly 551 does not have an optical junction alignment sleeve. Otherwise, except for the differences already noted, optical contact assemblies 642 and 551 are identical.

Receptacle optical contact block 543 is shorter than its plug counterpart 643. Typical optical junction 645b projects outward from the anterior end of contact block 543. When fully mated, optical junction 645b enters plug optical junction alignment sleeve 655, making face-to-face contact with plug optical junction 645a. It is desirable to have optical junctions mate with a predetermined face-to-face force when they are fully aligned both axially and rotationally. Springs 707a and 707b are slightly compressed when plug and receptacle 600, 500 are fully mated. That allows the face-to-face mating force to be predetermined, and also corrects for any axial stack-up uncertainties. (Alternatively, it would be possible to eliminate one of springs 707a, 707b; but for most applications using two springs is desirable.)

It is understood that the actual optical-contact type used can be one or a plurality of single-fiber contacts as shown here, or multiple-fiber contacts, as shown in U.S. patent application Ser. No. 12/212,870, published as US 2009-0080836, the disclosure of which is incorporated by reference, or some combination of diverse contact types.

Prior-art underwater-mateable connectors of the dual-chamber sort have a circular or annular passage created between opposed chambers when mated. Embodiments of the invention have a rectangular passage between opposed mated chambers, thereby facilitating economical, linear contact arrangements, and permitting simpler, more reliable sealing of the mated chambers;

In embodiments of the invention the sealing elements slide against each other, rather than stretch tightly around each other.

None of the invention's resilient end-seal elements are required to be distorted more than a very small amount, at most a few percent, to sealably seat to their adjoining parts. Many other wet-mateable connectors have elastomeric sealing elements that must stretch as much as 100%, or even more, to achieve proper seals. That exaggerated stretch decreases seal lifetime and performance, and can result in high mate-demate forces, and damaging "stiction" at sealing interfaces.

In the embodiments of the invention a wide choice of resilient or elastomeric sealing-element materials is available due to the modest mechanical requirements of the seals, thereby expanding the thermal and chemical limits of environments in which such connectors can be operated.

Embodiments of the invention provide a versatile "platform" into which a very wide range of optical and/or electrical or other junctions can be accommodated. Therefore once the platform has been qualified for use, changing contact configurations requires only minimal re-qualification.

There is essentially no limit to the size of the opening that can be created between the mated plug and receptacle units in the invention. The design is capable of being scaled up or down to meet diverse program requirements. Therefore the number and size of junctions that can be incorporated into the connector is not limited.

In embodiments of the invention, all of the various springs used in the plug and receptacle are contained in the benign fluids of their sealed chambers, diminishing the probability of corrosion.

As discussed above, although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

What is claimed is:

1. A coupler for sealably joining two reservoirs comprising:
   a receptacle having a forward end in communication with a respective reservoir, and having a longitudinal axis, wherein the receptacle is configured to couple its respective reservoir to a plug;
   a plug having a forward end in communication with a respective reservoir, and having a longitudinal axis, wherein the plug is configured to couple its respective reservoir to a receptacle, and wherein the receptacle and plug are movable between an unmated condition and a mated condition in which the forward end of the plug is in mating engagement with the forward end of the receptacle; and
   at least one movable seal member on the forward end of the receptacle, and at least one movable seal member on the forward end of the plug, wherein the respective at least one movable seal members move laterally between closed positions when the receptacle and plug are in the unmated condition and open positions when the receptacle and plug are in the mated condition.

2. The coupler according to claim 1, wherein the plug and receptacle forward ends each comprise a respective fixed seal member including a raised portion configured to receive the respective at least one movable seal member.

3. The coupler according to claim 2, wherein the raised portion of each respective fixed seal member comprises a slot, and wherein the respective at least one movable seal member is slidable laterally within the slot.

4. The coupler according to claim 3, wherein the slot has at least one interior surface which interfaces with at least one surface on the respective at least one movable seal member, and wherein the at least one movable seal member is in sealable engagement with its respective fixed seal member on all of the common interfaces with the slot in the unmated condition, and in sealable engagement with its respective fixed seal member on all common interfaces with the slot except for an opening created between the at least one movable seal member and the respective fixed seal member, in the mated condition.

5. The coupler according to claim 3, wherein each respective at least one movable seal member has a resilient portion, and wherein the resilient portion of each respective at least one movable seal member has a portion raised axially forward.

6. The coupler according to claim 3, wherein the raised portion of at least one of each of the plug and receptacle fixed seal members is resilient.

7. The coupler according to claim 4, wherein, in the unmated condition, the at least one movable receptacle seal member cooperates with the receptacle fixed seal member to sealably close the receptacle reservoir from the external environment.

8. The coupler according to claim 4, wherein, in the unmated condition, the at least one movable plug seal member cooperates with the plug fixed seal member to sealably close the plug reservoir from the external environment.

9. The coupler according to claim 6, wherein, upon mating, the raised portions of the plug fixed seal member and the respective raised portions of the receptacle fixed seal member are axially pressed together to seal their joined interface from the external environment.

10. The coupler according to claim 5, wherein upon mating, the raised portions of the at least one plug movable seal member and the respective raised portions of the at least one receptacle movable seal member are axially pressed together to seal their joined interface from the external environment.

11. The coupler according to claim 10, wherein the at least one movable seal member on the plug includes an axially extending actuator projection.

12. The coupler according to claim 11, wherein the at least one movable seal member on the receptacle includes a projection-receiving portion for receiving the plug actuator projection.

13. The coupler according to claim 10, wherein the at least one movable seal member on the receptacle moves laterally in unison with the at least one movable seal member on the plug when the at least one movable seal member of the plug is actuated between the closed and open positions.

14. The coupler according to claim 13, wherein, upon mating, the at least one receptacle movable seal member and the respective at least one plug movable seal member are axially pressed together to seal their joined interface from the external environment; and subsequently, while maintaining the sealed, joined interface, move laterally outward in unison from a closed position to an open position, thereby creating an open passage between the receptacle and plug reservoirs, said open passage being sealed from the external environment.

15. The coupler according to claim 13, wherein, upon de-mating, the at least one receptacle movable seal member and the respective at least one plug movable seal member are axially pressed together to seal their joined interface from the external environment; and subsequently, while maintaining the sealed, joined interface, move laterally inward in unison from an open position to a closed position, thereby sealing the open passage between the receptacle and plug reservoirs.

16. The coupler according to claim 1, wherein the at least one movable seal member on the forward end of the receptacle, and the at least one movable seal member on the forward end of the plug are biased to the closed position by a biasing member.

17. The coupler according to claim 16, wherein the biasing member is a spring.

18. The coupler according to claim 17, wherein the receptacle further comprises a back plate having a spring retaining bore configured to receive the biasing spring.

19. The coupler according to claim 17, wherein the plug further comprises a back plate having a spring retaining bore configured to receive the biasing spring.

20. The coupler according to claim 1, wherein the plug includes an actuator mechanism configured to actuate the at least one movable plug seal member from the closed position to the open position.

21. The coupler according to claim 20, wherein the actuator mechanism comprises an actuator stem with a tapered end.

22. The coupler according to claim 21, wherein the actuator stem includes one or a plurality of axial passages.

23. A coupler plug unit having an external shell, a longitudinal axis, an actuator stem, a forward end in communication with a respective reservoir and adapted for sealable engagement with a receptacle unit; the forward end comprising a longitudinal axis, an actuator pin, a fixed seal member, and at least one movable seal member; wherein the actuator stem is configured to actuate the at least one movable seal member from a closed position when the plug unit and the receptacle unit are in an unmated condition to an open position when the plug unit and the receptacle unit are in a mated condition, and wherein said plug forward end is movable between an axially forward position in the unmated condition and an axially inward position in the mated condition; and the actuator stem is an elongated element whose axial position is substantially fixed with respect to the external shell.

24. The coupler plug unit according to claim 23, wherein the forward end is slidable axially within the external shell.

25. The coupler plug unit according to claim 24, wherein the forward end is biased in the outward position by a biasing element.

26. The coupler plug unit according to claim 25, wherein the biasing element is a spring.

27. The coupler plug unit according to claim 23, wherein the actuator stem has a tapered end.

28. The coupler plug unit according to claim 23, wherein the actuator stem has a rectangular cross section.

29. The coupler plug unit according to claim 28, wherein the forward end is maintained in controlled rotational, tilt and axial alignment with the actuator stem by a controlled lateral fit between the actuator stem and a conformal through-port in the forward end.

30. The coupler plug unit according to claim 29 wherein lateral compliance of the forward end is provided by resilient nibs acting between the forward end and the external shell.

31. The coupler plug unit according to claim 23, wherein the actuator stem includes one or a plurality of axial passages.

32. The coupler plug unit according to claim 24, wherein the travel of the forward end towards the axially forward position is limited by a stop in the external shell.

33. The coupler plug unit according to claim 23, wherein the fixed seal member includes a portion raised in the axially forward direction.

34. The coupler plug unit according to claim 33, wherein the at least one movable seal member includes a portion raised in the axially forward direction.

35. The coupler plug unit according to claim 34, wherein the forward end is housed behind a protective end cap having openings to accommodate the raised portions of the fixed and movable seal members.

36. The coupler plug unit according to claim 33, wherein the at least one movable seal member is biased to the closed position by a biasing member.

37. The coupler plug unit according to claim 36, wherein the biasing member is a spring.

38. A coupler receptacle unit having an external shell, a longitudinal axis, and a forward end in communication with a respective reservoir, the forward end comprising a fixed seal element and at least one laterally-movable seal element configured to sealably engage a forward end of a coupler plug unit; wherein the forward end including the fixed seal element and the at least one movable seal element is held pressed against an interior wall of the forward end of the external shell by a biasing element.

39. The coupler receptacle unit according to claim 38, wherein the fixed seal element and the at least one movable seal element have portions raised in the axially forward direction.

40. The coupler receptacle unit according to claim 39 wherein the external shell comprises a front end having at least one opening to accommodate the raised portions of the fixed seal element and the at least one movable seal element.

41. The coupler receptacle unit according to claim 38, wherein the biasing element is a spring.

42. The coupler receptacle unit according to claim 41, wherein the biasing element accommodates axial stack-up tolerances of internal parts of the receptacle coupler unit.

43. The coupler receptacle unit according to claim 39, wherein the at least one movable seal member is biased to the closed position by a biasing member.

44. The coupler receptacle unit according to claim 43, wherein the biasing member is a spring.

45. A coupler receptacle unit having an external shell, a longitudinal axis, and a forward end in communication with a respective reservoir, the forward end comprising a fixed seal element and at least one laterally-movable seal element configured to sealably engage a forward end of a coupler plug unit, wherein the forward end is compliantly mounted within the external shell.

46. A coupler for sealably joining two reservoirs comprising: a plug unit in communication with a respective reservoir and having a longitudinal axis, an actuator stem, a forward projecting external shell, a forward end comprising an end cap, a fixed seal element and at least one movable seal element, said at least one movable seal element including an axially extending actuator projection, wherein the at least one movable seal element is movable from a closed position when the plug unit and a receptacle unit are in an unmated condition and an open position when the plug unit and a receptacle unit are in a mated condition, said plug forward end being axially movable within the plug external shell between an outward position in the unmated condition and an inward position in the mated condition; and a receptacle unit in communication with a respective reservoir and having a longitudinal axis, a forward end comprising a fixed seal element and at least one movable seal element, and an external shell with at least one front opening to accommodate the receptacle fixed seal element and the at least one movable seal element, said at least one movable seal element including an actuator receiving portion for receiving the plug actuator projection, and the actuator stem has a rectangular cross-section.

47. The coupler according to claim 46, in which the plug axially extending actuator projection is a pin.

48. The coupler according to claim 46, in which the receptacle actuator receiving portion for receiving the plug actuator projection is a socket.

49. A coupler for sealable joining two reservoirs comprising: a plug unit in communication with a respective reservoir and having a longitudinal axis, an actuator stem, a forward projecting external shell, a forward end comprising an end cap, a fixed seal element and at least one movable seal element, said at least one movable seal element including an axially extending actuator projection, wherein the at least one movable seal element is movable from a closed position when the plug unit and a receptacle unit are in an unmated condition and an open position when the plug unit and a receptacle unit are in a mated condition, said plug forward end being axially movable within the plug external shell between an outward position in the unmated condition and an inward position in the mated condition; and a receptacle unit in communication with a respective reservoir and having a longitudinal axis, a forward end comprising a fixed seal element and at least one movable seal element, and an external shell with at least one front opening to accommodate the receptacle fixed seal element and the at least one movable seal element, said at least one movable seal element including an actuator receiving portion for receiving the plug actuator projection, wherein, upon mating, the receptacle unit enters the forward projecting external plug shell, causing the receptacle fixed and at least one movable end seals to come into axial engagement with the respective plug fixed and at least one movable end seals, and further causing the plug axially extending actuator projection to engage the receptacle actuator receiving portion.

50. The coupler according to claim 49, wherein, upon substantial insertion of the receptacle unit into the external shell of the plug unit during mating of the coupler, the plug and receptacle forward ends each comprising a fixed seal element and at least one movable seal element move inward relative to the plug shell, thereby impaling said plug and receptacle forward ends upon the plug actuator stem and actuating the at least one movable plug seal laterally outward; while simultaneously moving the at least one receptacle movable seal laterally outward by way of the engagement of its plug-actuator-receiving portion with its respective plug movable-seal actuator projection, thus forming an opening between the plug fixed seal element and the at least one movable plug seal element and forming an opening between the receptacle fixed seal element and the at least one movable receptacle seal element to permit the plug actuator stem with axial passages to enter the receptacle reservoir and join the respective plug and receptacle reservoirs.

51. The coupler according to claim 50, in which the opening formed between the forward end plug fixed seal element and the at least one plug movable plug seal element when the at least one plug movable seal element moves laterally outward in the mated position is rectangular.

52. The coupler according to claim 51, wherein the rectangular opening formed between the plug fixed seal element and the at least one movable plug seal element when the at least one movable seal moves laterally outward in the mated condition sealably conforms to outer surfaces of the plug actuator stem.

53. The coupler according to claim 50, in which the opening formed between the receptacle end fixed seal element and the at least one movable receptacle seal element, when the at least one movable receptacle seal element moves laterally outward in the mated condition, is rectangular.

54. The coupler according to claim 53, wherein the rectangular opening formed between the receptacle fixed seal element and the at least one receptacle movable seal element, when the at least one movable seal element moves laterally outward in the mated condition, sealably conforms to outer surfaces of the plug actuator stem.

55. A coupler for sealably joining two closed reservoirs comprising: a plug unit in communication with a respective closed reservoir, and having a longitudinal axis, an actuator stem, a forward projecting external shell, a forward end comprising an end cap, a fixed seal element, at least one movable seal element including an axially extending actuator projection, wherein the at least one movable seal element is movable from a closed position when the plug unit and a receptacle unit are in an unmated position and an open position when the plug unit and a receptacle unit are in a mated condition, said plug forward end being axially movable within the plug external shell between an outward position in the unmated condition and an inward position in the mated condition; and a receptacle unit in communication with a respective closed reservoir, and having a longitudinal axis, a forward end comprising a fixed seal element and at least one movable seal element, and an external shell with at least one front opening to accommodate the receptacle fixed seal element and at least one movable seal element including an actuator receiving portion for receiving a plug actuator projection, and having in one of either the plug or receptacle closed reservoirs at least one first optical contact configured to receive a second optical contact in mating alignment, and in the other of either the plug or receptacle reservoirs a respective at least one second optical contact in mating alignment with said first optical contact, wherein when mated said respective at least one first and second optical contacts form an at least one optical circuit.

56. The coupler according to claim 55 in which the plug and receptacle closed reservoirs contain a mobile substance which is substantially optically transparent.

57. The coupler according to claim 56, in which at least one of the at least one plug or receptacle optical contacts is biased forward by a biasing element.

58. The coupler according to claim 57 in which the biasing element is a spring.

59. The coupler according to claim 55 in which at least one of the at least one plug or receptacle optical contacts is rotationally tunable.

60. A coupler for sealably joining two closed reservoirs comprising: a plug unit in communication with a respective closed reservoir, and having a longitudinal axis, an actuator stem, a forward projecting external shell, a forward end comprising an end cap, a fixed seal element, at least one movable seal element including an axially extending actuator projection, wherein the at least one movable seal element is movable from a closed position when the plug unit and a receptacle unit are in an unmated position and an open position when the plug unit and a receptacle unit are in a mated condition, said plug forward end being axially movable within the plug external shell between an outward position in the unmated condition and an inward position in the mated condition, and a receptacle unit in communication with a respective closed reservoir, and having a longitudinal axis, a forward end comprising a fixed seal element and at least one movable seal element, an external shell with at least one front opening to accommodate the receptacle fixed seal element and at least one movable seal element including an actuator receiving portion for receiving a plug actuator projection, wherein the closed plug and receptacle reservoirs each contain a mobile substance, and at least one of the closed plug and receptacle reservoirs incorporates a means to maintain the pressure within the closed reservoir substantially balanced to the in-situ exterior environment.

61. The coupler according to claim 60, in which the closed receptacle reservoir incorporates the means to maintain the pressure within the closed reservoir substantially balanced to the in-situ exterior environment.

62. The coupler according to claim 61, in which the means to maintain the pressure within the closed receptacle reservoir substantially balanced to the in-situ exterior environment comprises one or more flexible portions of the enclosure that defines the closed reservoir.

63. The coupler according to claim 60, in which the closed plug reservoir incorporates the means to maintain the pressure within the closed plug reservoir substantially balanced to the in-situ exterior environment.

64. The coupler according to claim 63, in which the means to maintain the pressure within the closed plug reservoir substantially balanced to the in-situ exterior environment comprises one or more flexible portions of the enclosure that defines the closed reservoir.

65. The coupler unit according to claim 62, having at least one or more optical and/or electrical contacts mounted within its respective closed reservoir.

66. The coupler according to claim 63, having at least one optical and/or electrical contact mounted within its respective closed reservoir for mating engagement to the respective at least one optical and/or electrical contact within the receptacle closed reservoir when the plug and receptacle coupler units are mated.

67. The coupler according to claim 60, having in one of either the plug or receptacle closed reservoirs at least one first electrical contact comprising a forward-extending pin with a conductive tip and a dielectric nipple around the base portion of the pin, and in the other of either the plug or receptacle reservoirs a respective at least one second electrical contact in mating alignment with said first electrical contact, said at least one second electrical contact comprising an electrical socket recessed in a dielectric bore sized to sealable fit to the dielectric nipple around the base portion of said respective first electrical pin, wherein when mated the engaged pin and socket form an electrical circuit, and the dielectric nipple and bore cooperate to seal the engaged contacts within a small entrapped volume of the reservoir mobile substance.

68. The coupler according to claim 67 in which the mobile substance within the plug and receptacle closed reservoirs is a dielectric substance.

69. The coupler according to claim 60, in which each of the plug and receptacle units contains at least one optical contact and at least one electrical contact.

70. The coupler according to claim 69 wherein the plug and receptacle reservoirs each contain a mobile substance which is dielectric and substantially transparent optically.

71. A method for sealably joining two reservoirs utilizing a plug unit and a receptacle unit each in communication with a respective reservoir, wherein the a plug unit comprises a forward end, an actuator stem, a fixed seal element and at least one movable seal element including an actuator projection, and wherein the receptacle unit comprises a forward end, a fixed seal element and at least one movable seal element including an actuator projection receiving portion, the method comprising: moving the receptacle unit and plug unit from an unmated condition to a mated condition in which the forward end of the plug unit is in mating engagement with the forward end of the receptacle unit; receiving the plug actuator projection in the receptacle actuator projection receiving portion; impaling the plug and receptacle forward ends with the plug actuator stem; moving the at least one plug movable seal element and the at least one receptacle movable seal element laterally outward by the plug actuator stem from a closed position when the plug unit and a receptacle unit are in the unmated condition and an open position when the plug unit and a receptacle unit are in the mated condition.

72. The method according to claim 71, wherein the plug unit and the receptacle unit each further comprise an external shell, wherein the forward end of each of the plug unit and the receptacle unit is axially movable within their respective shell; the method further comprising moving the plug forward end axially within plug external shell between and outward position in the unmated condition and an inward condition in the mated condition.

73. The method according to claim 71, wherein the plug unit and the receptacle unit each include at least one optical and/or electrical contact, the method further comprising matingly engaging respective at least one optical and/or electrical contacts.

* * * * *